US008332038B2

(12) United States Patent
Heruth et al.

(10) Patent No.: US 8,332,038 B2
(45) Date of Patent: Dec. 11, 2012

(54) DETECTING SLEEP TO EVALUATE THERAPY

(75) Inventors: Kenneth T. Heruth, Edina, MN (US); Keith A. Miesel, St. Paul, MN (US); Jonathan C. Werder, Corcoran, MN (US); Steve R. LaPorte, Arden Hills, MN (US); Nina M. Graves, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/249,862

(22) Filed: Sep. 30, 2011

(65) Prior Publication Data
US 2012/0022340 A1 Jan. 26, 2012

Related U.S. Application Data

(63) Continuation of application No. 11/691,405, filed on Mar. 26, 2007, now Pat. No. 8,055,348, which is a continuation-in-part of application No. 11/081,786, filed on Mar. 16, 2005, now Pat. No. 7,775,993, which is a continuation-in-part of application No. 10/825,964, filed on Apr. 15, 2004, now abandoned.

(60) Provisional application No. 60/553,771, filed on Mar. 16, 2004, provisional application No. 60/785,822, filed on Mar. 24, 2006.

(51) Int. Cl.
*A61N 1/08* (2006.01)
(52) U.S. Cl. .................................................. 607/45
(58) Field of Classification Search .............. 607/2, 41, 607/48, 45
See application file for complete search history.

(56) References Cited

U.S. PATENT DOCUMENTS

| 4,297,685 | A | 10/1981 | Brainard, II |
| 4,550,736 | A | 11/1985 | Broughton et al. |
| 4,771,780 | A | 9/1988 | Sholder |
| 4,776,345 | A | 10/1988 | Cohen et al. |
| 4,846,195 | A | 7/1989 | Alt |

(Continued)

FOREIGN PATENT DOCUMENTS

DE 198 31 109 1/2000

(Continued)

OTHER PUBLICATIONS

Amzica, "Physiology of Sleep and Wakefulness as it Relates to the Physiology of Epilepsy," Journal of Clinical Neurophysiology, American Clinical Neurophysiology Society, 19(6), pp. 488-503, (2002).

(Continued)

*Primary Examiner* — Carl H Layno
*Assistant Examiner* — Paula J Stice
(74) *Attorney, Agent, or Firm* — Shumaker & Sieffert, PA

(57) ABSTRACT

A system includes one or more sensors and a processor. Each of the sensors generates a signal as a function of at least one physiological parameter of a patient that may discernibly change when the patient is asleep. The processor monitors the physiological parameters, and determines whether the patient is asleep based on the parameters. In some embodiments, the processor determines plurality of sleep metric values, each of which indicates a probability of the patient being asleep, based on each of a plurality of physiological parameters. The processor may average or otherwise combine the plurality of sleep metric values to provide an overall sleep metric value that is compared to a threshold value in order to determine whether the patient is asleep. In addition, an electroencephalogram signal may be used to identify sleep states of the patient.

30 Claims, 10 Drawing Sheets

U.S. PATENT DOCUMENTS

| | | |
|---|---|---|
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,299,118 A | 3/1994 | Martens et al. |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,713,923 A | 2/1998 | Ward et al. |
| 5,732,696 A | 3/1998 | Rapoport et al. |
| 5,782,884 A | 7/1998 | Stotts et al. |
| 5,833,709 A | 11/1998 | Rise et al. |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 5,999,846 A | 12/1999 | Pardey et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,227,203 B1 | 5/2001 | Rise et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,597,954 B1 | 7/2003 | Pless et al. |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 7,162,304 B1 | 1/2007 | Bradley |
| 7,209,787 B2 | 4/2007 | DiLorenzo |
| 7,787,946 B2 | 8/2010 | Stahmann et al. |
| 2001/0031930 A1 | 10/2001 | Roizen et al. |
| 2001/0037067 A1 | 11/2001 | Tchou et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0135917 A1 | 7/2003 | Ruane |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0204219 A1 | 10/2003 | Gielen |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0085738 A1 | 4/2005 | Stahmann et al. |
| 2005/0113710 A1 | 5/2005 | Stahmann et al. |
| 2005/0119703 A1 | 6/2005 | DiLorenzo |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | DiLorenzo |
| 2006/0293720 A1 | 12/2006 | DiLorenzo |
| 2007/0073355 A1 | 3/2007 | DiLorenzo |
| 2007/0142862 A1 | 6/2007 | DiLorenzo |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Dinner, "Effect of Sleep on Epilepsy," Journal of Clinical Neurophysiology, American Clinical Neurophysiology Society, 19(6), pp. 504-513, (2002).

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).

Mendez et al. "Interactions Between Sleep and Epilepsy," Journal of Clinical Neurophysiology, American Clinical Neurophysiology Society, 18(2), pp. 106-127, (2001).

"MiniMitter® Physiological and Behavioral Monitoring for Humans and Animals," http://www.minimitter.com/Products/Actiwatch, 3 pgs. Feb. 20, 2006.

"IBM & Citzen Watch develop Linux-based 'WatchPad'," 5 pgs., http://www.linuxdevices.com/news/NS6580187845.html, Feb. 20, 2006.

"Design Competition: Runners-Up for the Best Three Designs," EPN, vol. 26, No. 1, 1 pg., (2002).

"Watch," Wikipedia, the free encyclopedia, 6 pgs., http://en.wikipedia.org/wiki/Watch, Feb. 20, 2006.

Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.

Tuisku, "Motor Activity Measured by Actometry in Neuropsychiatric Disorders," Department of Psychiatry, University of Helsinki, Helsinki, Finland, 115 pgs. (2002).

Smith et al., "Presleep Cognitions in Patients with Insomnia Secondary to Chronic Pain," Journal of Behavioral Medicine, vol. 24, No. 1, pp. 93-114, (2001).

Smith et al. "How do sleep disturbance and chronic pain inter-relate? Insights from the longitudinal and cognitive-behavioral clinical trials literature," Sleep Medicine Reviews, YSMRV 286, pp. 1-14, (2003).

Goodrich et al., "The Prediction of Pain Using Measures of Sleep Quality," Pain Digest, 8:23-25, (1998).

"Analysis of heart rate dynamics by methods derived from nonlinear mathematics: Clinical applicability and prognostic significance" http:/herkules.oulu.fi.isbn9514250133/html, 4 pgs., (2004).

Kerr et al., "Analysis of the sit-stand-sit movement cycle in normal subjects," Clinical Biomechanics, vol. 12, No. 4, pp. 236-245, (1997).

Aminian et al. "Physical Activity Monitoring Based on Accelerometry: Validation and Comparison with Video Observation," Medical & Biological Engineering & Computing, vol. 37, No. 2, pp. 304-308 (1999).

Medcare—A Global Leader in Sleep Diagnostics, Embletta Recording System, http://www.medcare.com/products/diagnostic/embletta/, 2 pgs. Jan. 31, 2005.

Medcare—A Global Leader in Sleep Diagnostics, Somnologica for Embletta, http://www.medcare.com/products/diagnostic/embletta/SomnoEmbletta/index.asp, 1 pg. Jan. 31, 2005.

MAP Medizin-Technologie GmbH, Poly-MESAM®, http://195.244.124.130/map/de/eng/map_med.nsf/smsall/70564A3FCBE4188AC1256EF4.., 4 pgs. Jan. 31, 2005.

Merlin, http://www.aha.ru/~pir/english/merlin/, 4 pgs. Jan. 31, 2005.

Sleep Solutions—PR Newswire: Sleep Solutions Introduces NovaSom™ QSG™ for PSG.., http://www.sleep-solutions.com/press_room/novasom.htm, 2 pgs. Jan. 31, 2005.

Itamar Medical Information, http://itamar-medical.com/content.asp?id-id=31, 2 pgs. Jan. 31, 2005.

Criticare System Inc.,-504DX Portable Pulse Oximeter, http://www.csiusa.com/504dx.html, 4 pgs. Jan. 31, 2005.

Snap® Laboratories, Product Fact Sheet, http://www.snaplab.com/mp_fact.htm, 2 pgs. Jan. 31, 2005.

Sleep Strip & Bite Strip, http://ww.quietsleep.com/snoringapnea/sleepstrip.htm , 8 pgs. Jan. 31, 2005.

"Bitestrip Flier," downloaded from Internet Archive of www.quietsleep.com dated Jan. 29, 2005 http://web.archive.org/web/20041124080003/www.quietsleep.com/pdf/Bitestrip+Flier.pdf.

"Bilateral Comparisons of the BiteStrip Bruxism Device and Masseter EMG Bruxism Events" downloaded from Internet Archive of www.quietsleep.com dated Jan. 29, 2005 http://web.archive.org/web/20041124075114/www.quietsleep.com/pdf/Bilateral+Comparisons.pdf.

"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.

Office Action dated Nov. 13, 2008 for U.S. Appl. No. 11/081,786 (7 pgs.).

Sazonov et al., "Activity-based sleep-wake identification in infants," Institute of Physics Publishing, Physiological Measurement, 25, pp. 1291-1304, Aug. 11, 2004.

Office Action dated Jul. 22, 2008 for U.S. Appl. No. 11/081,786 (12 pgs.).

Responsive Amendment dated Sep. 22, 2008 for U.S. Appl. No. 11/081,786 (10 pgs.).

Advisory Action dated Oct. 15, 2008 for U.S. Appl. No. 11/081,786 (3 pgs.).

Responsive Amendment dated Aug. 7, 2008 for U.S. Appl. No. 11/081,857 (13 pgs.).

Response dated Aug. 22, 2008 for U.S. Appl. No. 10/826,925 (7 pgs.).

Responsive Amendment dated Aug. 29, 2008 for U.S. Appl. No. 11/081,811 (13 pgs.).

Office Action dated May 28, 2010 for U.S. Appl. No. 11/410,448 (13 pgs.).

Responsive Amendment dated Aug. 27, 2010 for U.S. Appl. No. 11/410,448 (23 pgs.).

Office Action dated Mar. 23, 2009 for U.S. Appl. No. 10/825,964 (8 pgs.).

Responsive Amendment dated May 26, 2009 for U.S. Appl. No. 10/825,964 (7 pgs.).

Office Action dated Apr. 21, 2009 for U.S. Appl. No. 11/081,786 (12 pgs.).

Responsive Amendment dated Jun. 22, 2009 for U.S. Appl. No. 11/081,786 (8 pgs.).

Office Action dated May 5, 2008 for U.S. Appl. No. 10/826,925 (12 pgs.).

Office Action dated May 30, 2008 for U.S. Appl. No. 11/081,811 (13 pgs.).

Office Action dated May 6, 2008 for U.S. Appl. No. 10/825,955 (13 pgs.).

Response to Office Action dated Jul. 2, 2008 for U.S. Appl. No. 10/825,955 (13 pgs.).

Office Action dated May 9, 2008 for U.S. Appl. No. 11/081,857 (10 pgs.).

Office Action dated Dec. 12, 2008 for U.S. Appl. No. 11/081,811 (12 pgs.).

Responsive Amendment dated Mar. 12, 2009 for U.S. Appl. No. 11/081,811 (13 pgs.).

Responsive Amendment dated Feb. 13, 2009 for U.S. Appl. No. 11/081,786 (8 pgs.).

Office Action dated Sep. 5, 2008 for U.S. Appl. No. 10/825,964 (6 pgs.).

Office Action dated Nov. 6, 2008 for U.S. Appl. No. 11/081,857 (8 pgs.).

Responsive Amendment dated Jan. 5, 2009 for U.S. Appl. No. 10/825,964 (13 pgs.).

Response dated Jan. 6, 2009 for U.S. Appl. No. 11/081,857 (6 pgs.).

Office Action dated Feb. 17, 2011 for U.S. Appl. No. 11/691,405, (9 pgs.).

Responsive Amendment dated May 17, 2011 for U.S. Appl. No. 11/691,405, (14 pgs.).

Office Action dated Nov. 9, 2012 for U.S. Appl. No. 11/691,376, (30 pgs.).

Responsive Amendment dated Feb. 8, 2012 for U.S. Appl. No. 11/691,376, (17 pgs.).

Cicolin et al., "Effects of deep brain stimulation of the subthalamic nucleus on sleep architecture in parkinsonian patients," Sleep Medicine, vol. 5, Issue 2, pp. 207-210, Mar. 2004.

Oerlemans et al., "The prevalence of sleep disorders in patients with Parkinson's disease. A self-reported, community-based survey," Sleep Medicine, vol. 3, Issue 2, pp. 147-149, Mar. 2002.

Antonini et al., "Deep brain stimulation and its effect on sleep in Parkinson's disease," Sleep Medicine, vol. 5, Issue 2, pp. 211-214, Mar. 2004.

Final Office Action dated Mar. 19, 2012 for U.S. Appl. No. 11/691,376, (37 pgs.).

Office Action dated May 3, 2012 for U.S. Appl. No. 12/544,727, (10 pgs.).

Final Office Action dated Mar. 1, 2012 for U.S. Appl. No. 11/591,286, (31 pgs.).

Responsive Amendment dated May 1, 2012 for U.S. Appl. No. 11/591,286, (16 pgs.).

Responsive Amendment dated Jun. 15, 2012 for U.S. Appl. No. 11/691,376, (17 pgs.).

Responsive Amendment dated Jul. 31, 2012 for U.S. Appl. No. 12/544,727, (12 pgs.).

Office Action dated Jul. 5, 2012 for U.S. Appl. No. 11/591,286, (34 pgs.).

Greenberg et al., "Mechanisms and the Current State of Deep Brain Stimulation in Neuropsychiatry," CNS Spectrums, vol. 8, No. 7, pp. 522-526, Jul. 2003.

DETECTING SLEEP TO EVALUATE THERAPY

This application is a continuation of U.S. application Ser. No. 11/691,405, filed Mar. 26, 2007, now issued as U.S. Pat. No. 8,055,348 which is a continuation-in-part of U.S. application Ser. No. 11/081,786, filed Mar. 16, 2005, now issued as U.S. Pat. No. 7,775,993, which is a continuation-in-part of U.S. application Ser. No. 10/825,964, filed Apr. 15, 2004, now abandoned, which claims the benefit of U.S. provisional application No. 60/553,771, filed Mar. 16, 2004. U.S. application Ser. No. 11/691,405, filed Mar. 26, 2007 also claims the benefit of U.S. Provisional Application No. 60/785,822, filed Mar. 24, 2006. The entire content of each of these applications is incorporated herein by reference.

TECHNICAL FIELD

The invention relates to medical devices, and to techniques for determining whether a patient is asleep.

BACKGROUND

The ability to determine whether a patient is asleep is useful in a variety of medical contexts. In some situations, the ability to determine whether a patient is asleep is used to diagnose conditions of the patient. For example, the amount of time that patients sleep, the extent of arousals during sleep, and the times of day that patients sleep have been used to diagnose sleep apnea. Such sleep information could also be used to diagnose psychological disorders, such as depression, mania, bipolar disorder, or obsessive-compulsive disorder.

In other situations, a determination as to whether a patient is asleep is used to control delivery of therapy to the patient. For example, neurostimulation or drug therapies can be suspended when the patient is asleep, or the intensity/dosage of the therapies can be reduced when a patient is asleep. As another example, the rate response settings of a cardiac pacemaker may be adjusted to less aggressive settings when the patient is asleep so that the patient's heart will not be paced at an inappropriately high rate during sleep. In these examples, therapy may be suspended or adjusted when the patient is asleep to avoid patient discomfort, or to conserve a battery and/or contents of a fluid reservoir of an implantable medical device when the therapy may be unneeded or ineffective. However, in other cases, a therapy intended to be delivered when the patient is asleep, such as therapy intended to prevent or treat sleep apnea, is delivered based on a determination that the patient is asleep. Other ailments that may negatively affect patient sleep quality include movement disorders, such as tremor, Parkinson's disease, multiple sclerosis, epilepsy, or spasticity, as well as sleep apnea, congestive heart failure, gastrointestinal disorders and incontinence. All of these disorders may be generally classified as neurological disorders.

Existing techniques for determining whether a patient is asleep include monitoring the electroencephalogram (EEG) of the patient to identify brain wave activity indicative of sleep. However, EEG monitoring typically requires that an array of electrodes be placed on a patient's scalp and coupled to an external monitoring device, and is most often performed in a clinic setting. Generally, an implantable medical device may only be used to monitor a patient's EEG in the rare cases when it is coupled to electrodes implanted within the brain of the patient. Consequently, existing EEG monitoring techniques are generally unsuitable for determining whether a patient is asleep in order to control therapy, or for long-term monitoring of the patient's sleep/wake cycle.

Existing techniques employed by implantable medical devices to determine whether a patient is asleep include monitoring the patient's respiration rate, respiration rate variability, and activity level. Each of these physiological parameters may be an inaccurate indicator of whether a patient is asleep. For example, from the perspective of these physiological parameters, it may appear that a patient is sleeping when, instead, the patient is merely lying down in a relaxed state. As another example, respiration rate and respiration rate variability, for example, may fail to accurately indicate that the patient is asleep when the patient suffers from a breathing disorder, such as Cheyne-Stokes syndrome.

SUMMARY

In general, the invention is directed to techniques for determining whether a patient is asleep. In some embodiments, the invention is directed to techniques that involve determination of values of one or more sleep metrics that indicate a probability of a patient being asleep based on the current value of one or more physiological parameters of the patient. Use of a plurality of sleep metrics, in particular, may allow for a more accurate determination of whether a patient is asleep.

A system according to the invention includes one or more sensors and a processor. Each of the sensors generates a signal as a function of at least one physiological parameter of a patient that may discernibly change when the patient is asleep. Exemplary physiological parameters include activity level, posture, heart rate, electrocardiogram (ECG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response.

The processor monitors the physiological parameters based on the signals generated by the sensors, and determines whether the patient is asleep based on values for the physiological parameters. The value for a physiological parameter may be a current, mean or median value for the parameter. In some embodiments, the processor may additionally or alternatively determine whether the patient is asleep based on the variability of one or more of the physiological parameters.

In some embodiments, the processor determines a value of a sleep metric that indicates a probability of the patient being asleep based on a physiological parameter. In particular, the processor may apply a function or look-up table to the current value and/or variability of the physiological parameter to determine the sleep metric value. The processor may compare the sleep metric value to a threshold value to determine whether the patient is asleep. In some embodiments, the processor may compare the sleep metric value to each of a plurality of thresholds to determine the current sleep state of the patient, e.g., rapid eye movement (REM), or one of the nonrapid eye movement (NREM) states (S1, S2, S3, S4). Because they provide the most "refreshing" type of sleep, the ability to determine whether the patient is in one of the S3 and S4 sleep states may be, in some embodiments, particularly useful.

Further, in some embodiments the processor may determine a sleep metric value for each of a plurality of physiological parameters. In other words, the processor may apply a function or look-up table for each parameter to the current value for that parameter in order to determine the sleep metric value for that parameter. The processor may average or otherwise combine the plurality of sleep metric values to provide an overall sleep metric value for comparison to the threshold values. In some embodiments, a weighting factor may be applied to one or more of the sleep metric values. One or more of functions, look-up tables, thresholds and weighting factors may be selected or adjusted by a user in order to select or adjust the sensitivity and specificity of the system in determining whether the patient is asleep.

In some embodiments, the processor may determine whether the patient is asleep, at least in part, by analyzing an electroencephalogram (EEG) of the patient. For example, the processor may determine whether the patient is asleep based on the frequency, e.g., predominant frequency, in the EEG. Further, the processor may determine in which sleep state (S1-S4 and REM) the patient is based on what frequency or range of frequencies are evident in the EEG.

In some embodiments, the processor is included as part of a medical device, such as an implantable medical device. The sensors may also be included within the medical device, coupled to the medical device by one or more leads, or in wireless communication with the medical device. The medical device may control delivery of therapy to the patient based on the determination as to whether the patient is asleep, or may store information indicating when the patient is asleep for later retrieval and analysis by user. In some embodiments, the medical device may instead use the one or more sleep metric values to control delivery of therapy, or may store one or more sleep metric values. In some embodiments, information relating to the patient's sleep patterns may be used to diagnose sleep disorders, chronic pain, and neurological disorders that include movement and psychological disorders. Example disorders may include Parkinson's disease, tremor, multiple sclerosis, spasticity, or epilepsy. Information relating to the patient's sleep patterns may also be used to diagnose cardiac disorders such as congestive heart failure or arrhythmia, or psychological disorders such as depression, mania, bipolar disorder, or obsessive-compulsive disorder. Further, information relating to a patient's sleep patterns may be used to evaluate the effectiveness of a therapy delivered to the patient to treat any of these ailments or symptoms.

In one embodiment, the invention is directed to a method for evaluating the efficacy of at least one of a movement disorder therapy, psychological disorder therapy, or deep brain stimulation which includes monitoring at least physiological parameter of a patient via an implantable medical device that delivers the at least one of the movement disorder therapy, psychological disorder therapy, or deep brain stimulation to the patient, monitoring sleep patterns of the patient with the implantable medical device based on the physiological parameter, and presenting sleep quality information to a user based on the sleep patterns for evaluation of the efficacy of the at least one of the movement disorder therapy, psychological disorder therapy, or deep brain stimulation.

In another embodiment, the invention is directed to a medical system that includes a sensor that generates a signal as a function of at least one physiological parameter of a patient, and an implantable medical device that delivers at least one of a movement disorder therapy, psychological disorder therapy, or deep brain stimulation, monitors the at least one physiological parameter of the patient based on the signal output by the sensor, and monitors sleep patterns of the patient based on the physiological parameter. The system further comprises a computing device that provides sleep quality information based on the sleep patterns for evaluation of the efficacy of the at least one of the movement disorder therapy, psychological disorder therapy, or deep brain stimulation.

In an additional embodiment, the invention is directed to a system that includes means for monitoring at least physiological parameter of a patient via an implantable medical device that delivers the at least one of the movement disorder therapy, psychological disorder therapy, or deep brain stimulation to the patient, means for monitoring sleep patterns of the patient with the implantable medical device based on the physiological parameter, and means for presenting sleep quality information to a user based on the sleep patterns for evaluation of the efficacy of the at least one of the movement disorder therapy, psychological disorder therapy, or deep brain stimulation.

The invention may be capable of providing one or more advantages. For example, the invention provides techniques for determining a sleep state of a patient that may be implemented in an implantable medical device. Further, the techniques provided by the invention may include analysis of a variety of physiological parameters not previously used in determining whether a patient is asleep. Where it is desired to detect sleep via an implantable medical device, the ability to determine whether a patient is sleeping based on these physiological parameters may increase the number of implantable medical device types in which the invention may be implemented, i.e., the invention may be implemented in a variety of types of implantable medical devices which include or may be easily modified to include sensors capable of generating a signal based on such physiological parameters.

Monitoring a plurality of physiological parameters according to some embodiments, rather than a single parameter, may allow for a more accurate determination of whether a patient is asleep than is available via existing implantable medical devices. Use of sleep metrics that indicate a probability of the patient being asleep for each of a plurality of physiological parameters may further increase the reliability with which an implantable medical device may determine whether a patient is asleep. In particular, rather than a binary sleep or awake determination for each of a plurality of parameters, sleep metric values for each of a plurality of parameters may be combined to yield an overall sleep metric value that may be compared to a threshold to determine whether the patient is asleep. In other words, failure of any one physiological parameter to accurately indicate whether a patient is sleeping may be less likely to prevent the implantable medical device from accurately indicating whether the patient is sleeping when considered in combination with other physiological parameters.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
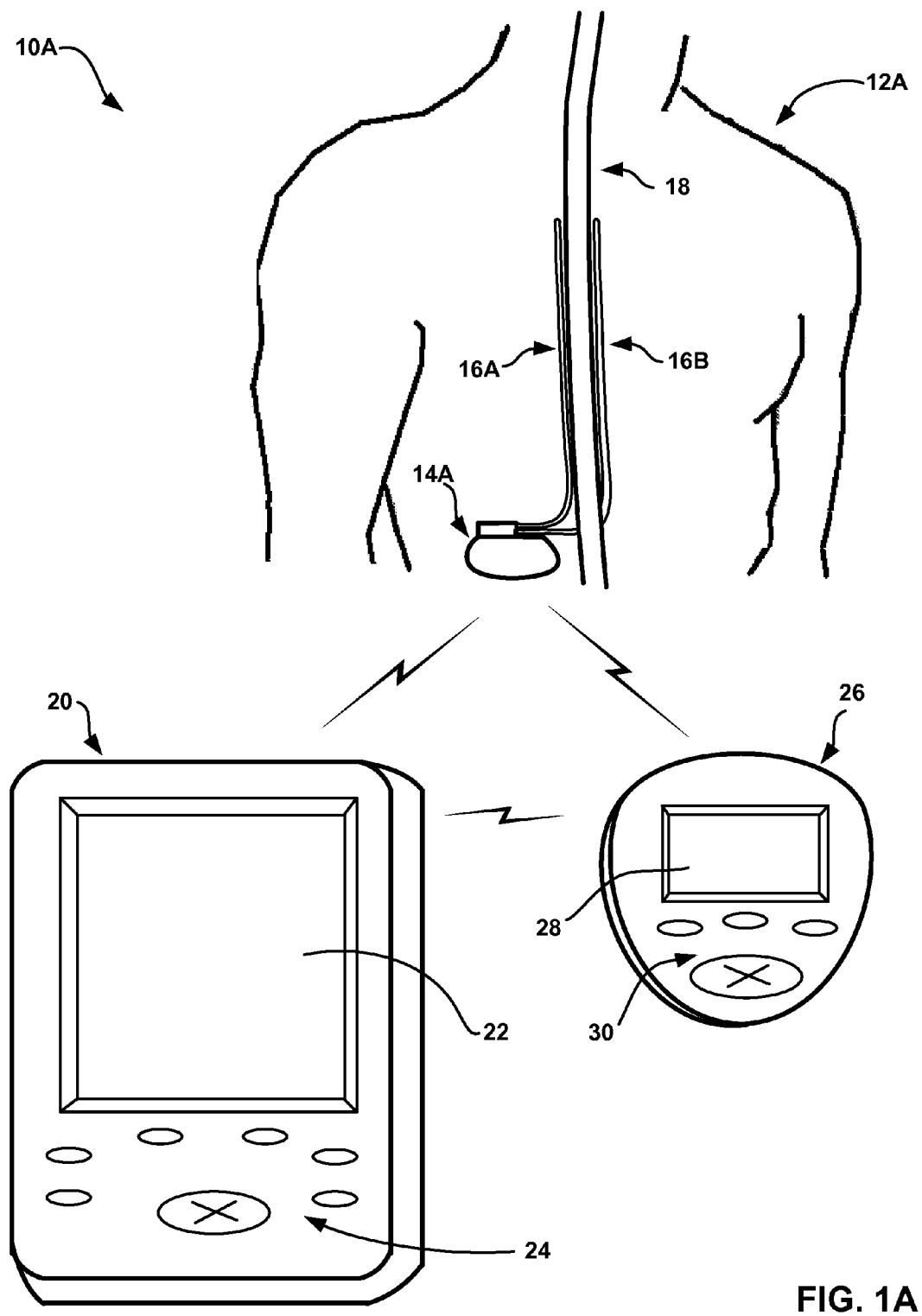
FIGS. 1A and 1B are conceptual diagrams illustrating example systems including an implantable medical device that determines whether a patient is asleep according to the invention.
Figure 1B:
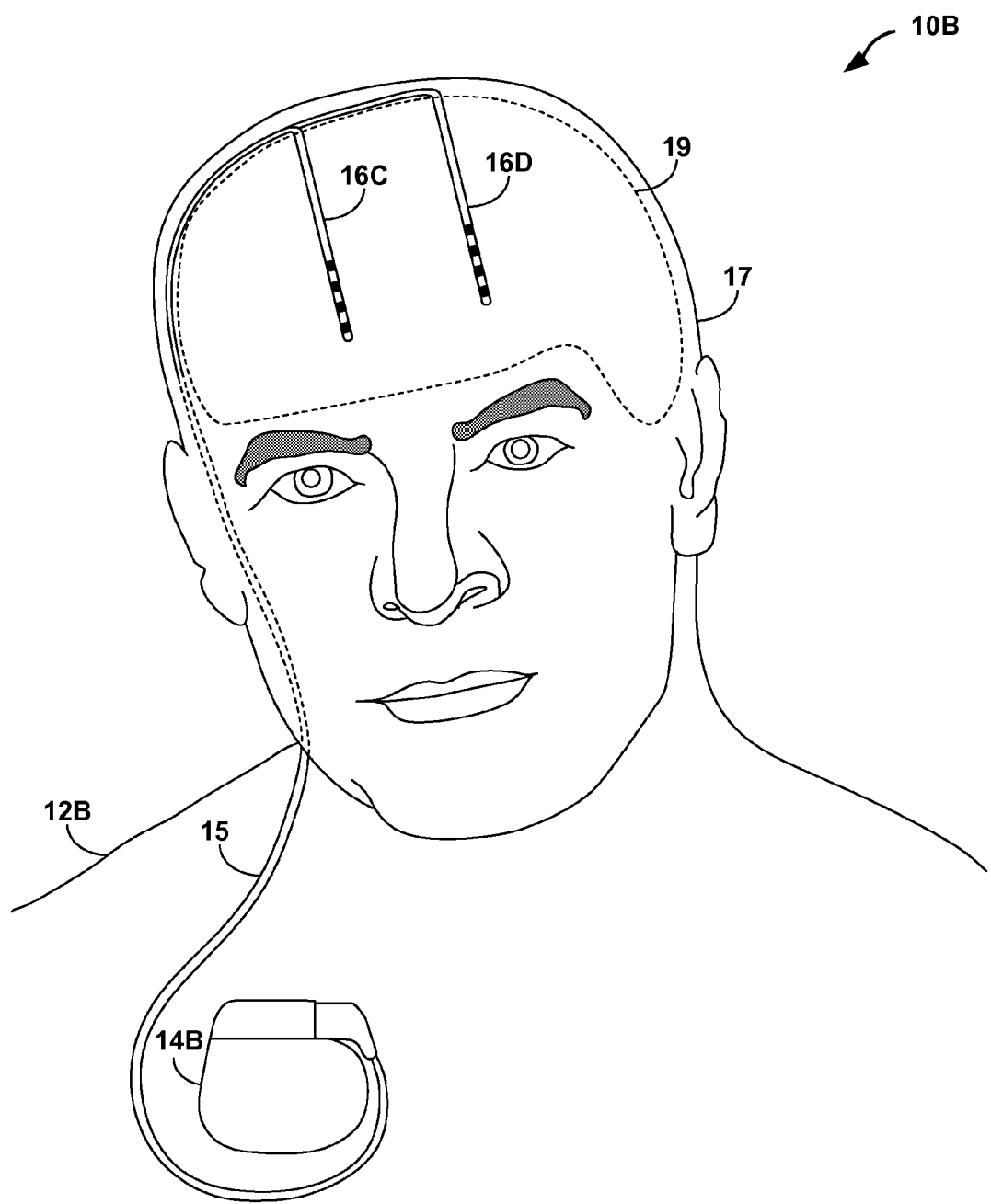

FIGS. 1A and 1B are conceptual diagrams illustrating example systems 10A and 10B (collectively "systems 10") that respectively include an implantable medical device (IMD) 14A or 14B (collectively "IMDs 14") that determine whether a respective one of patients 12A and 12B (collectively "patients 12") is asleep according to the invention. In the illustrated example system, IMDs 14 take the form of an implantable neurostimulator that delivers neurostimulation therapy in the form of electrical pulses to patients 12. However, the invention is not limited to implementation via an implantable neurostimulator, or even to implementation via IMDs.

For example, in some embodiments of the invention, IMDs 14 may take the form of an implantable pump or implantable cardiac pacemaker may determine whether a patient is asleep. In other embodiments, the medical device that determines when patients 12 are asleep may be an implantable or external patient monitor. Further, a programming device or other computing device may determine when patients 12 is asleep based on information collected by a medical device. In other words, any implantable or external device may determine whether a patient is asleep according to the invention.

In the illustrated example systems 10, IMDs 14 respectively deliver neurostimulation therapy to patients 12A and 12B via leads 16A and 16B, and leads 16C and 16D (collectively "leads 16"), respectively. Leads 16A and 16B may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16A and 16B shown in FIG. 1A or the delivery of SCS or other pain therapies.

For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. Example therapies may treat tremor, Parkinson's disease, spasticity, epilepsy, depression or obsessive-compulsive disorder. Non-respiratory neurological disorders exclude respiratory disorders, such as sleep apnea. As illustrated in FIG. 1B, leads 16C and 16D may be coupled to IMD 14B via one or more lead extensions 15.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of lead implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

IMDs 14 deliver therapy according to a set of therapy parameters that define the delivered therapy. In embodiments where IMDs 14 delivers neurostimulation therapy in the form of electrical pulses, the parameters for each of the parameter sets may include voltage or current pulse amplitudes, pulse widths, pulse rates, and the like. Further, each of leads 16 includes electrodes (not shown in FIG. 1), and the parameters may include information identifying which electrodes have been selected for delivery of pulses, and the polarities of the selected electrodes. In embodiments in which IMDs 14 deliver other types of therapies, therapy parameter sets may include other therapy parameters such as drug concentration and drug flow rate in the case of drug delivery therapy.

Each of systems 10 may also includes a clinician programmer 20 (illustrated as part of system 10A in FIG. 1A). A clinician (not shown) may use clinician programmer 20 to program neurostimulation therapy for patient 12A. Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus, mouse, or the like. Keypad 24 may take the form of an alphanumeric keypad or a reduced set of keys associated with particular functions.

Systems 10 also includes a patient programmer 26 (illustrated as part of system 10A in FIG. 1A), which also may, as shown in FIG. 1A, be a handheld computing device. Patient 12A may use patient programmer 26 to control the delivery of neurostimulation therapy by IMD 14A. Patient programmer 26 may also include a display 28 and a keypad 30, to allow patient 12A to interact with patient programmer 26. In some embodiments, display 26 may be a touch screen display, and patient 12A may interact with patient programmer 26 via display 28. Patient 12A may also interact with patient programmer 26 using peripheral pointing devices, such as a stylus or mouse.

IMDs 14, clinician programmer 20 and patient programmer 26 may, as shown in FIG. 1A, communicate via wireless communication. Clinician programmer 20 and patient programmer 26 may, for example, communicate via wireless communication with IMD 14A using RF telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14A and patient programmer 26 via remote telemetry techniques known in the art, communicating via a local area network (LAN), wide area network (WAN), public switched telephone network (PSTN), or cellular telephone network, for example.

As mentioned above, IMDs 14 are capable of determining whether patients 12 are asleep. Specifically, as will be described in greater detail below, IMDs 14 monitor a plurality of physiological parameters of patients 12 that may discernibly change when patients 12 are asleep, and determines whether patients 12 are asleep based on values of the physiological parameters. The value for a physiological parameter may be a current, mean or median value for the parameter. In some embodiments, IMDs 14 may additionally or alternatively determine whether a patient 12 is asleep based on the variability of one or more of the physiological parameters. IMDs 14 include, are coupled to, or are in wireless communication with one or more sensors, and monitor the physiological parameters via the sensors.

Exemplary physiological parameters that may be monitored by IMDs 14 include activity level, posture, heart rate, electrocardiogram (ECG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity (such as an electroencephalogram or EEG), and eye motion (such as an electrooculogram or EOG). In some external medical device embodiments of the invention, galvanic skin response may additionally or alternatively be monitored. Some of the parameters, such as activity level, heart rate, some ECG morphological features, respiration rate, respiratory volume, blood pressure, arterial oxygen saturation and partial pressure, partial pressure of oxygen in the cerebrospinal fluid, muscular activity and tone, core temperature, subcutaneous temperature, arterial blood flow, and galvanic skin response may be at low values when a patient 12 is asleep. Further, the variability of at least some of these parameters, such as heart rate and respiration rate, may be at a low value when the patient is asleep. Information regarding the posture of a patient 12 will most likely indicate that a patient 12 is lying down when a patient 12 is asleep.

In some embodiments, IMDs 14 determine a value of one or more sleep metrics based on a value of one or more physiological parameters of a patient 12. A sleep metric value may be a numeric value that indicates the probability that a patient 12 is asleep. In some embodiments, the sleep metric value may be a probability value, e.g., a number within the range from 0 to 1.

In particular, IMDs 14 may apply a function or look-up table to the current, mean or median value, and/or the variability of the physiological parameter to determine a value of the sleep metric. IMDs 14 may compare the sleep metric value to a threshold value to determine whether the patient is asleep. In some embodiments, IMDs 14 may compare the sleep metric value to each of a plurality of thresholds to determine the current sleep state of the patient, e.g., rapid eye movement (REM), S1, S2, S3, or S4. Because they provide the most "refreshing" type of sleep, the ability to determine whether the patient is in one of the S3 and S4 sleep states may be, in some embodiments, particularly useful.

Further, in some embodiments IMDs 14 may determine a sleep metric value for each of a plurality of physiological parameters. In other words, IMDs 14 may apply a function or look-up table for each parameter to a value for that parameter in order to determine the sleep metric value for that parameter. IMDs 14 may average or otherwise combine the plurality of sleep metric values to provide an overall sleep metric value for comparison to the threshold values. In some embodiments, IMDs 14 may apply a weighting factor to one or more of the sleep metric values prior to combination. One or more of functions, look-up tables, thresholds and weighting factors may be selected or adjusted by a user, such as a clinician via programmer 20 or a patient 12 via programmer 26, in order to select or adjust the sensitivity and specificity of IMDs 14 in determining whether a patient 12 is asleep.

Monitoring a plurality of physiological parameters according to some embodiments, rather than a single parameter, may allow IMDs 14 to determine whether a patient 12 is asleep with more accuracy than existing implantable medical devices. Use of sleep metric values that indicate a probability of the patient being asleep for each of a plurality of physiological parameters may further increase the accuracy with which IMDs 14 may determine whether a patient 12 is asleep. In particular, rather than a binary sleep or awake determination for each of a plurality of parameters, sleep metric values for each of a plurality of parameters may be combined to yield an overall sleep metric value that may be compared to a threshold to determine whether a patient 12 is asleep. In other words, failure of any one physiological parameter to accurately indicate whether a patient is sleeping may be less likely to prevent IMDs 14 from accurately indicating whether a patient 12 is sleeping when considered in combination with other physiological parameters.

In some embodiments, the IMDs 14 may determine whether the patient is asleep, at least in part, by analyzing an electroencephalogram (EEG) of the patient. For example, the IMDs 14 may determine whether the patient is asleep based on the amplitude or frequency, e.g., predominant frequency, in the EEG. Further, the IMDs 14 may determine in which sleep state (S1-S4 and REM) the patient is based on what frequency or range of frequencies are evident in the EEG.

IMDs 14 may control delivery of therapy to a patient 12 based on the determination as to whether the patient 12 is asleep. For example, IMDs 14 may suspend delivery of neurostimulation or reduce the intensity of delivered neurostimulation when a patient 12 is determined to be asleep. In other embodiments, IMDs 14 may suspend or reduce intensity of drug delivery, or may reduce the aggressiveness of rate response for cardiac pacing when a patient 12 is determined to be asleep. In still other embodiments, IMDs 14 may initiate delivery of a therapy, such as a therapy to treat or prevent sleep apnea, when a patient 12 is determined to be asleep.

In some embodiments, IMDs 14 store information indicating when a patient 12 is asleep, which may be retrieved for analysis by a clinician via programmer 20, for example. The clinician may use the sleep information to diagnose conditions of a patient 12, such as sleep apnea or psychological disorders, such as depression, mania, bipolar disorder, or obsessive-compulsive disorder. Information relating to the sleep patterns of a patient 12 may in other situations indicate the effectiveness of a delivered therapy and/or the need for increased therapy. Some ailments of a patient 12, such as chronic pain, movement disorders such as tremor, Parkinson's disease, multiple sclerosis, or spasticity, psychological disorders, gastrointestinal disorders, incontinence, congestive heart failure, and sleep apnea may disturb or hinder the sleep or a patient 12, or, in some cases, inadequate or disturbed sleep may increase the symptoms of these ailments.

IMDs 14 may collect information relating to the sleep patterns of a patient 12, which may be retrieved by a clinician or patient 12 via programmer 20, 26 and used to evaluate the effectiveness of a therapy delivered to the patient 12 for such an ailment, or to indicate the need for an additional therapy to improve the sleep pattern of the patient 12. In some embodiments, IMDs 14 may determine when a patient is attempting to sleep based on an indication via a user interface of, for example, a programming device, or monitored physiological parameters. IMDs 14 may also determine when a patient is asleep based on monitoring physiological parameters as described herein. With such information, the IMDs 14 may determine, as examples, the percentage of time a patient was asleep when trying to sleep, or sleep efficiency, and the amount of time required for the patient to fall asleep, or sleep latency.

Additionally, the IMDs 14 may track the total time sleeping per day, time spent in deeper sleep states, e.g., S3 and S4, or a number of arousal events during sleep, using the techniques described herein for identifying whether a patient is asleep and in which sleep state a patient is. Each of these sleep quality metrics may reflect the quality of sleep experienced by a patient, and thereby indicate the effectiveness of a therapy or a particular parameter set for the therapy. The IMDs 14 may associate values for such metrics with the therapy delivered, or therapy parameter set used to control delivery of the therapy, at the time when the value was determined, for the purpose of allowing a user to evaluate the therapies or parameter sets. In some cases, IMDs 14 may evaluate such collected sleep information and automatically adjust a therapy for such a condition based on the evaluation.

Further information regarding evaluation of a therapy based on sleep information collected by an IMD may be found in a commonly-assigned and copending U.S. patent application Ser. No. 11/691,376 by Ken Heruth and Keith Miesel, entitled "COLLECTING SLEEP QUALITY INFORMATION VIA A MEDICAL DEVICE," which was filed on Mar. 26, 2007. Further information regarding automatic control of a therapy based on sleep information collected by an IMD may be found in a commonly-assigned and copending U.S. patent application Ser. No. 11/691,430 by Ken Heruth and Keith Miesel, entitled "CONTROLLING THERAPY BASED ON SLEEP QUALITY," which was filed on Mar. 26, 2007. The entire content of both of these applications is incorporated herein by reference.

Figure 2A:
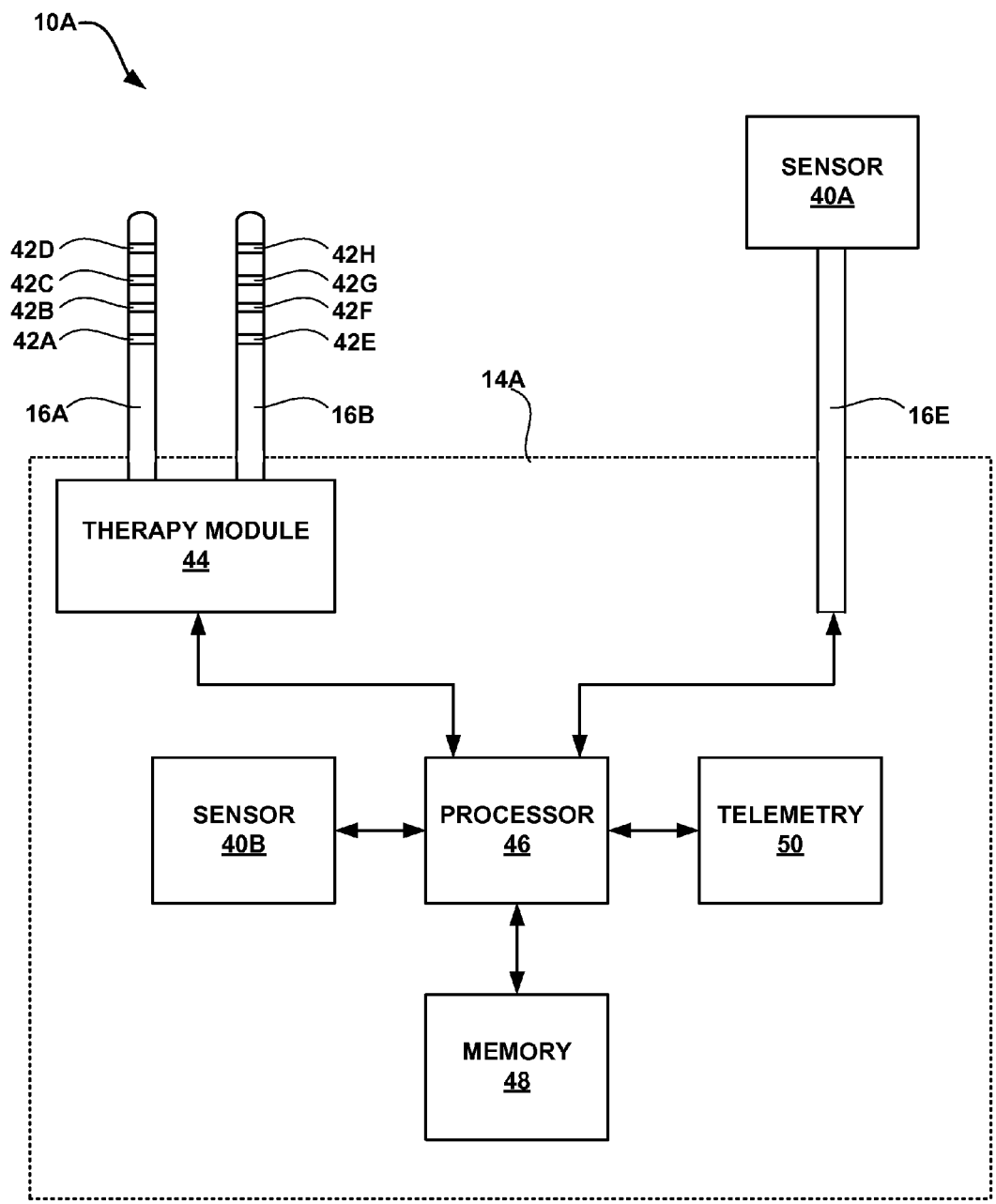
FIGS. 2A and 2B are block diagrams further illustrating the example systems and implantable medical devices of FIGS. 1A and 1B.
Figure 2B:
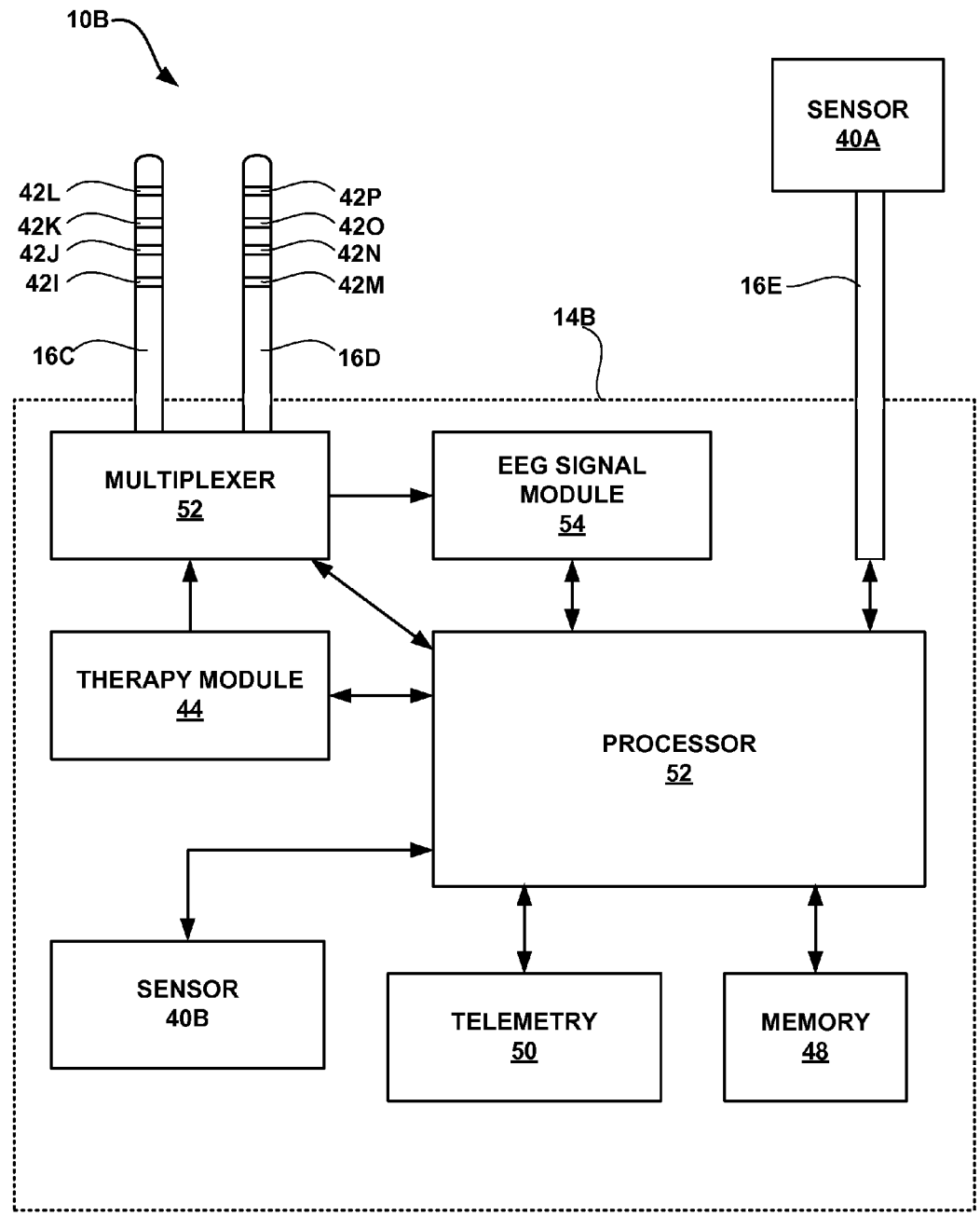

FIGS. 2A and 2B are block diagrams further illustrating systems 10A and 10B. In particular, FIG. 2A illustrates an example configuration of IMD 14A and leads 16A and 16B. FIG. 2B illustrates an example configuration of IMD 14B and leads 16C and 16D. FIGS. 2A and 2B also illustrate sensors 40A and 40B (collectively "sensors 40") that generate signals as a function of one or more physiological parameters of patients 12. IMDs 14 monitor the signals to determine whether patient 12 is asleep.

IMD 14A may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 42"). Electrodes 42 may be ring electrodes. The configuration, type and number of electrodes 42 illustrated in FIGS. 2A and 2B are merely exemplary. For example, leads 16 may each include eight electrodes 42, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include a pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to a set of therapy parameters, which may be one of a plurality of therapy parameter sets stored in memory 48. However, the invention is not limited to implantable neurostimulator embodiments or even to IMDs that deliver electrical stimulation. For example, in some embodiments a therapy delivery module 44 of an IMD may include a pump, circuitry to control the pump, and a reservoir to store a therapeutic agent for delivery via the pump.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause IMD 14 and processor 46 to perform the functions attributed to them herein.

Each of sensors 40 generates a signal as a function of one or more physiological parameters of a patient 12. Although shown as including two sensors 40, systems 10 may include any number of sensors. As illustrated in FIGS. 2A and 2B, sensors 40 may be included as part of IMDs 14, or coupled to IMDs 14 via leads 16. Sensors 40 may be coupled to IMDs 14 via therapy leads 16, or via other leads 16, such as lead 16E depicted in FIGS. 2A and 2B. In some embodiments, a sensor located outside of IMDs 14 may be in wireless communication with processor 46. Wireless communication between sensors 40 and IMDs 14 may, as examples, include RF communication or communication via electrical signals conducted through the tissue and/or fluid of a patient 12.

As discussed above, exemplary physiological parameters of a patient 12 that may be monitored by IMDs 14 to determine values of one or more sleep metrics include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, and eye motion. Further, as discussed above, in some external medical device embodiments of the invention galvanic skin response may additionally or alternatively be monitored. The detected values of these physiological parameters of a patient 12 may discernibly change when the patient 12 falls asleep or wakes up. Some of these physiological parameters may be at low values when patient 12 is asleep. Further, the variability of at least some of these parameters, such as heart rate and respiration rate, may be at a low value when the patient is asleep. Sensors 40 may be of any type known in the art capable of generating a signal as a function of one or more of these parameters.

For example, sensors 40 may include electrodes located on leads or integrated as part of the housing of IMDs 14 that generate an electrogram signal as a function of electrical activity of the heart of a patient 12, and processor 46 may monitor the heart rate of the patient 12 based on the electrogram signal. In other embodiments, a sensor may include an acoustic sensor within IMDs 14, a pressure or flow sensor within the bloodstream or cerebrospinal fluid of a patient 12, or a temperature sensor located within the bloodstream of the patient 12. The signals generated by such sensors may vary as a function of contraction of the heart of a patient 12, and can be used by IMDs 14 to monitor the heart rate of a patient 12.

In some embodiments, processor 46 may detect, and measure values for one or more ECG morphological features within an electrogram generated by electrodes as described above. ECG morphological features may vary in a manner that indicates whether a patient 12 is asleep or awake. For example, the amplitude of the ST segment of the ECG may decrease when a patient 12 is asleep. Further, the amplitude of QRS complex or T-wave may decrease, and the widths of the QRS complex and T-wave may increase when a patient 12 is asleep. The QT interval and the latency of an evoked response may increase when a patient 12 is asleep, and the amplitude of the evoked response may decrease when the patient 12 is asleep.

Sensors 40 may include one or more accelerometers, gyros, mercury switches, or bonded piezoelectric crystals that generate a signal as a function of patient activity, e.g., body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running or the like. The electrodes may be coupled to IMDs 14 wirelessly or by leads 16 or, if IMDs 14 are implanted in these locations, integrated with a housing of IMDs 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to IMDs 14 wirelessly or via leads 16, or piezoelectric crystals may be bonded to the can of IMDs 14 when the IMDs are implanted in these areas, e.g., in the back, buttocks, chest, or abdomen of a patient 12.

Processor 46 may also detect spasmodic, irregular, movement disorder or pain related muscle activation via the signals generated by such sensors. Such muscle activation may indicate that a patient 12 is not sleeping, e.g., unable to sleep, or if a patient 12 is sleeping, may indicate a lower level of sleep quality.

Sensors 40 may also include a plurality of accelerometers, gyros, or magnetometers oriented orthogonally that generate signals that indicate the posture of a patient 12. In addition to being oriented orthogonally with respect to each other, each of sensors 40 used to detect the posture of a patient 12 may be generally aligned with an axis of the body of the patient 12. When accelerometers, for example, are aligned in this manner, the magnitude and polarity of DC components of the signals generate by the accelerometers indicate the orientation of the patient relative to the Earth's gravity, e.g., the posture of a patient 12. Further information regarding use of orthogonally aligned accelerometers to determine patient posture may be found in a commonly-assigned U.S. Pat. No. 5,593,431, which issued to Todd J. Sheldon.

Other sensors 40 that may generate a signal that indicates the posture of a patient 12 include electrodes that generate an electromyogram (EMG) signal, or bonded piezoelectric crystals that generate a signal as a function of contraction of muscles. Such sensors 40 may be implanted in the legs, buttocks, chest, abdomen, or back of a patient 12, as described above. The signals generated by such sensors when implanted in these locations may vary based on the posture of a patient 12, e.g., may vary based on whether the patient is standing, sitting, or lying down.

Further, the posture of a patient 12 may affect the thoracic impedance of the patient. Consequently, sensors 40 may include an electrode pair, including one electrode integrated with the housing of IMDs 14 and one of electrodes 42, that generates a signal as a function of the thoracic impedance of a patient 12, and processor 46 may detect the posture or posture changes of the patient 12 based on the signal. The electrodes of the pair may be located on opposite sides of the patient's thorax. For example, the electrode pair may include one of electrodes 42 located proximate to the spine of a patient for delivery of SCS therapy, and IMD 14 with an electrode integrated in its housing may be implanted in the abdomen of a patient 12.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to IMDs 14 wirelessly or via leads 16. CSF pressure changes associated with posture changes may be particularly evident within the brain of the patient, e.g., may be particularly apparent in an intracranial pressure (ICP) waveform.

The thoracic impedance of a patient 12 may also vary based on the respiration of the patient 12. Consequently, in some embodiments, an electrode pair that generates a signal as a function of the thoracic impedance of a patient 12 may be used to detect respiration of the patient 12. In other embodiments, sensors 40 may include a strain gauge, bonded piezoelectric element, or pressure sensor within the blood or cerebrospinal fluid that generates a signal that varies based on patient respiration. An electrogram generated by electrodes as discussed above may also be modulated by patient respiration, and may be used as an indirect representation of respiration rate.

Sensors 40 may include electrodes that generate an electromyogram (EMG) signal as a function of muscle electrical activity, as described above, or may include any of a variety of known temperature sensors to generate a signal as a function of a core subcutaneous temperature of a patient 12. Such electrodes and temperature sensors may be incorporated within the housing of IMDs 14, or coupled to IMDs 14 wirelessly or via leads. Sensors 40 may also include a pressure sensor within, or in contact with, a blood vessel. The pressure sensor may generate a signal as a function of the a blood pressure of a patient 12, and may, for example, comprise a Chronicle Hemodynamic Monitor™ commercially available from Medtronic, Inc. of Minneapolis, Minn. Further, certain muscles of a patient 12, such as the muscles of the patient's neck, may discernibly relax when patient 12 is asleep or within certain sleep states. Consequently, sensors 40 may include strain gauges or EMG electrodes implanted in such locations that generate a signal as a function of muscle tone.

Sensors 40 may also include optical pulse oximetry sensors or Clark dissolved oxygen sensors located within, as part of a housing of, or outside of IMDs 14, which generate signals as a function of blood oxygen saturation and blood oxygen partial pressure respectively. In some embodiments, systems 10 may include a catheter with a distal portion located within the cerebrospinal fluid of a patient 12, and the distal end may include a Clark sensor to generate a signal as a function of the partial pressure of oxygen within the cerebrospinal fluid. Embodiments in which an IMD comprises an implantable pump, for example, may include a catheter with a distal portion located in the CSF.

In some embodiments, sensors 40 may include one or more intraluminal, extraluminal, or external flow sensors positioned to generate a signal as a function of arterial blood flow. A flow sensor may be, for example, an electromagnetic, thermal convection, ultrasonic-Doppler, or laser-Doppler flow sensor. Further, in some external medical device embodiments of the invention, sensors 40 may include one or more electrodes positioned on the skin of patient 12 to generate a signal as a function of galvanic skin response.

Additionally, in some embodiments, sensors 40 may include one or more electrodes positioned within or proximate to the brain of patient, which detect electrical activity of the brain. For example, in embodiments in which IMDs 14 delivers stimulation or other therapy to the brain, processor 46 may be coupled to electrodes implanted on or within the brain via a leads 16. System 10B, illustrated in FIGS. 1B and 2B, is an example of a system that includes electrodes 42, located on or within the brain of patient 12B, that are coupled to IMD 14B.

As shown in FIG. 2B, electrodes 42 may be selectively coupled to therapy module 44 or an electroencephalogram (EEG) signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable by processor 46, as well as suitable filter and amplifier circuitry.

Processor 46 may also direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

In other embodiments, processor 46 may be wirelessly coupled to electrodes that detect brain electrical activity. For example, one or more modules may be implanted beneath the scalp of the patient, each module including a housing, one or more electrodes, and circuitry to wirelessly transmit the signals detected by the one or more electrodes to IMDs 14. In other embodiments, the electrodes may be applied to the patient's scalp, and electrically coupled to a module that includes circuitry for wirelessly transmitting the signals detected by the electrodes to IMDs 14. The electrodes may be glued to the patient's scalp, or a head band, hair net, cap, or the like may incorporate the electrodes and the module, and may be worn by a patient 12 to apply the electrodes to the patient's scalp when, for example, the patient is attempting to sleep. The signals detected by the electrodes and transmitted to IMDs 14 may be EEG signals, and processor 46 may identify the amplitude and or frequency of the EEG signals as physiological parameter values.

Also, the motion of the eyes of a patient 12 may vary depending on whether the patient is sleeping and which sleep state the patient is in. Consequently, sensors 40 may include electrodes place proximate to the eyes of a patient 12 to detect electrical activity associated with motion of the eyes, e.g., to generate an electro-oculography (EOG) signal. Such electrodes may be coupled to IMDs 14 via one or more leads 16, or may be included within modules that include circuitry to wirelessly transmit detected signals to IMDs 14. Wirelessly coupled modules incorporating electrodes to detect eye motion may be worn externally by a patient 12, e.g., attached to the skin of the patient 12 proximate to the eyes by an adhesive when the patient is attempting to sleep.

Processor 46 may monitor one or more of these physiological parameters based on the signals generated by the one or more sensors 40, and determine whether a patient 12 is attempting to sleep or asleep based on current values for the physiological parameters. In some embodiments, processor 46 may determine mean or median value for the parameter based on values of the signal over time, and determines whether a patient 12 is asleep based on the mean or median value. In other embodiments, processor 46 may additionally or alternatively determine a variability of one or more of the parameters based on the values of the parameter over time, and may determine whether a patient 12 is asleep based on the one or more variability values. IMDs 14 may include circuitry (not shown) that conditions the signals generate by sensors 40 such that they may be analyzed by processor 46. For example, IMDs 14 may include one or more analog to digital converters to convert analog signals generate by sensors 40 into digital signals usable by processor 46, as well as suitable filter and amplifier circuitry.

In some embodiments, processor 46 determines a value of a sleep metric that indicates a probability of the patient being asleep based on a physiological parameter. In particular, processor 46 may apply a function or look-up table to the current value, mean or median value, and/or variability of the physiological parameter to determine the sleep metric value. For example, the values of one or more physiological parameters serve as indices to the lookup table to yield a corresponding output value, which serves as the sleep metric value. Processor 46 may compare the sleep metric value to a threshold value to determine whether a patient 12 is asleep. In some embodiments, processor 46 may compare the sleep metric value to each of a plurality of thresholds to determine the current sleep state of a patient 12, e.g., rapid eye movement (REM), S1, S2, S3, or S4.

Further, in some embodiments processor 46 determines a sleep metric value for each of a plurality of monitored physiological parameters. In other words, processor 46 may apply a function or look-up table for each parameter to the current value for that parameter in order to determine the sleep metric value for that individual parameter. Processor 46 may then average or otherwise combine the plurality of sleep metric values to provide an overall sleep metric value, and may determine whether a patient 12 is asleep based on the overall sleep metric value. In some embodiments, processor 46 may apply a weighting factor to one or more of the sleep metric values prior to combination.

In some embodiments, the processor 46 may determine whether the patient is asleep, at least in part, by analyzing an electroencephalogram (EEG) of the patient. For example, the processor 46 may determine whether the patient is asleep based on the amplitude or frequency, e.g., predominant frequency, in the EEG. Further, the processor 46 may determine in which sleep state (S1-S4 and REM) the patient is based on what frequency or range of frequencies are evident in the EEG.

Figure 3:
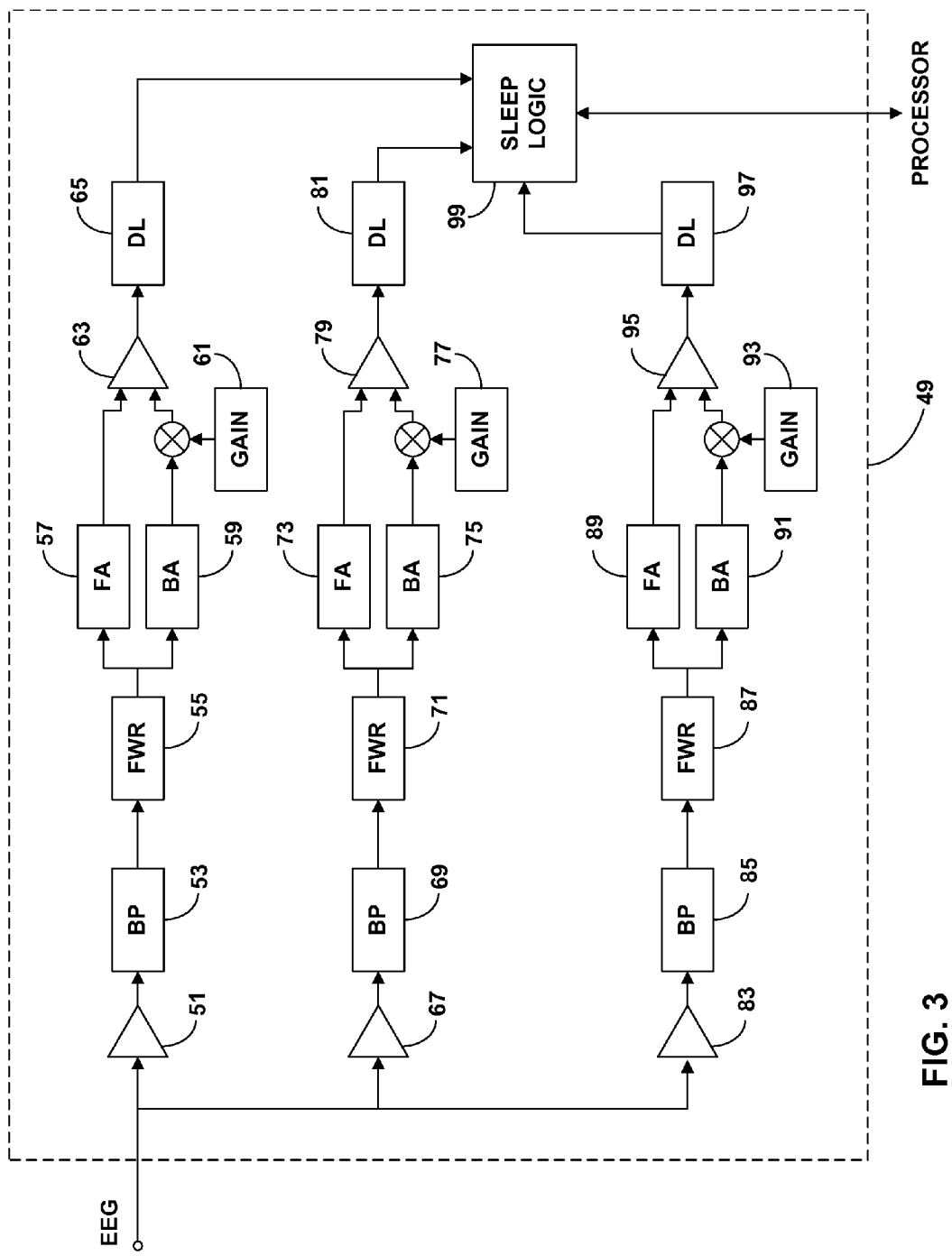
FIG. 3 is a logic diagram illustrating an example circuit that detects the sleep state of a patient from the electroencephalogram (EEG) signal.

FIG. 3 is a logical diagram of an example circuit that detects whether a patient is asleep and/or the sleep type of a patient based on the electroencephalogram (EEG) signal. As shown in FIG. 3, module 49 may be integrated into an EEG signal module of IMDs 14 or a separate implantable or external device capable of detecting an EEG signal. An EEG signal detected by electrodes adjacent to the brain of a patent 12 is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85.

Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then processed to identify in which sleep state a patient 12 is in.

After bandpass filtering of the original EEG signal, the filtered signals are similarly processed in parallel before being delivered to sleep logic module 99. For ease of discussion, only one of the three channels will be discussed herein, but each of the filtered signals would be processed similarly.

Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that patient 12 may be within the S1 or S2 sleep states. In some embodiments, as least duration logic 65, 81, 97 and sleep logic 99 may be embodied in a processor of the device containing EEG module 49.

Module 49 may detect all sleep types for a patient 12. Further, the beginning of sleep may be detected by module 49 based on the sleep state of a patient 12. Some of the components of module 49 may vary from the example of FIG. 3. For example, gains 61, 77 and 93 may be provided from the same power source. Module 49 may be embodied as analog circuitry, digital circuitry, or a combination thereof.

In other embodiments, FIG. 3 may not need to reference the background average to determine the current state of sleep of a patient 12. Instead, the power of the signals from bandpass filters 53, 69 and 85 are compared to each other, and sleep logic module 99 determines which the sleep state of patient 12 based upon the frequency band that has the highest power. In this case, the signals from full-wave rectifiers 55, 71 and 87 are sent directly to a device that calculates the signal power, such as a spectral power distribution module (PSD), and then to sleep logic module 99 which determines the frequency band of the greatest power, e.g., the sleep state of a patient 12.

In some cases, the signal from full-wave rectifiers 55, 71 and 87 may be normalized by a gain component to correctly weight each frequency band.

Figure 4:
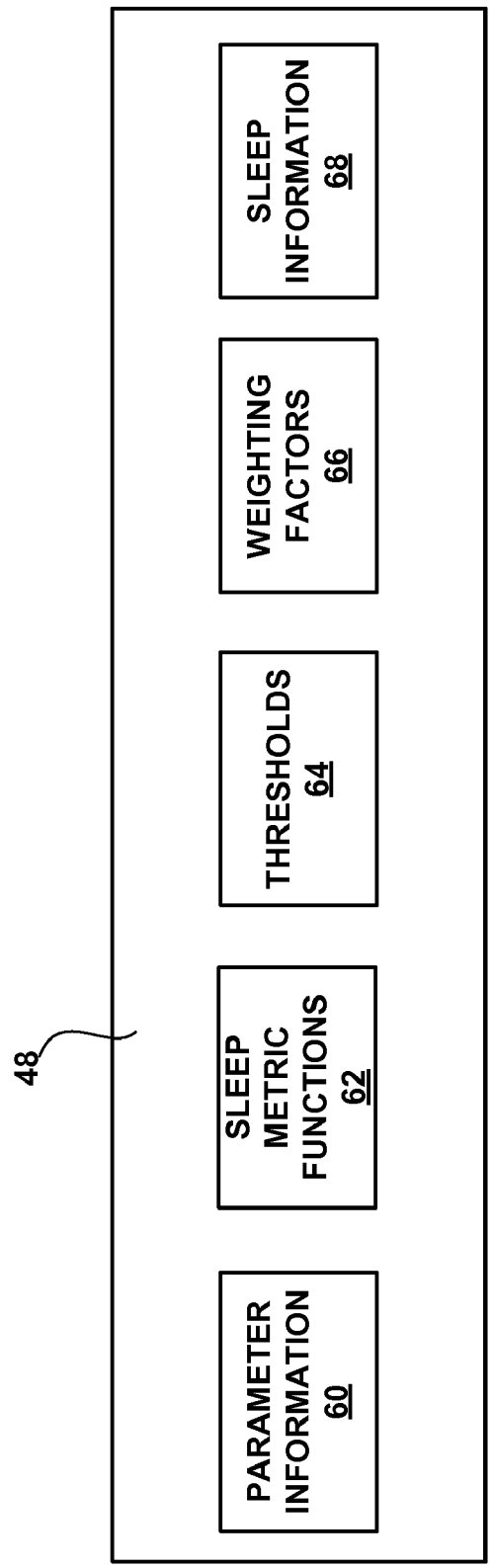
FIG. 4 is a block diagram illustrating a memory within an implantable medical device of the system of FIG. 1.

As shown in FIG. 4, memory 48 may include parameter information 60 recorded by processor 46, e.g., parameter values, or mean or median parameter values. Memory 48 may also store sleep metric functions 62 or look-up tables (not shown) that processor 46 may retrieve for application to physiological parameter values or variability values, and threshold values 64 that processor 46 may use to determine whether a patient 12 is asleep and, in some embodiments, the sleep state of a patient 12. Memory 48 may also store weighting factors 66 used by processor 46 when combining sleep metric values to determine an overall sleep metric value. Processor 46 may store sleep information 68 within memory 48, such as recorded sleep metric values and information indicating when patient 12 was asleep.

As shown in FIGS. 2A and 2B, IMDs 14 also includes a telemetry circuit 50 that allows processor 46 to communicate with clinician programmer 20 and patient programmer 26. For example, using clinician programmer 20, a clinician may direct processor 46 to retrieve sleep information 68 from memory 48 and transmit the information via telemetry circuit 50 to programmer 20 for analysis. Further, the clinician may select or adjust the one or more of functions 62, look-up tables, thresholds 64 and weighting factors 66 in order to select or adjust the sensitivity and specificity of processor 46 determining whether the patient is asleep.

Figure 5:
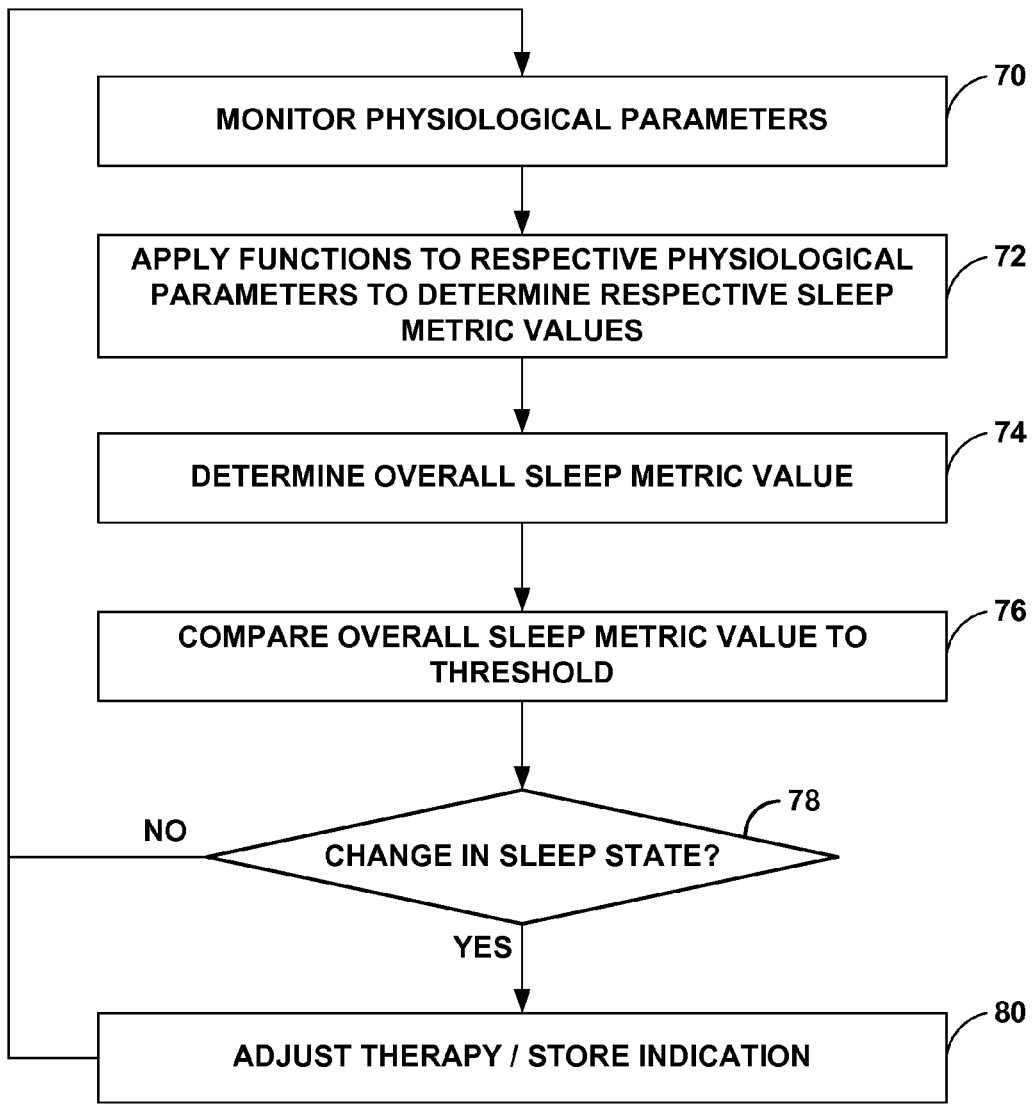
FIG. 5 is a flowchart illustrating an example technique for determining whether a patient is asleep.

FIG. 5 is a flowchart illustrating an example technique for determining whether a patient is asleep that may be employed by IMDs 14. According to the example technique, IMDs 14 monitors a plurality of physiological parameters of a patient 12 (70). More particularly, processor 46 receives signals from one or more sensors 40, and monitors the physiological parameters based on the signals.

Processor 46 applies a respective function 62 to current values, mean or median values, and/or variability values for each of physiological parameters to determine a sleep metric value for each of the parameters (72). Processor 46 then combines the various sleep metric values to determine a current overall sleep metric value (74). For example processor 46 may apply weighting factors 66 to one or more of the parameter specific sleep metric values, and then average the parameter specific sleep metric values in light of the weighting factors 66.

Processor 46 compares the current overall sleep metric value to a threshold value 64 (76), and determines whether a patient 12 is asleep or awake, e.g., whether the sleep state of the patient 12 has changed, based on the comparison (78). For example, processor 46 may determine that a patient 12 is asleep if the current overall sleep metric value exceeds the threshold value 64. If the sleep state of a patient 12 has changed, processor 46 may initiate, suspend or adjust a therapy delivered to the patient 12 by IMDs 14, or processor 46 may store an indication of the time and the change within memory 48 (80), e.g., for use in evaluation of therapy or therapy parameter sets as described above.

Figure 6:
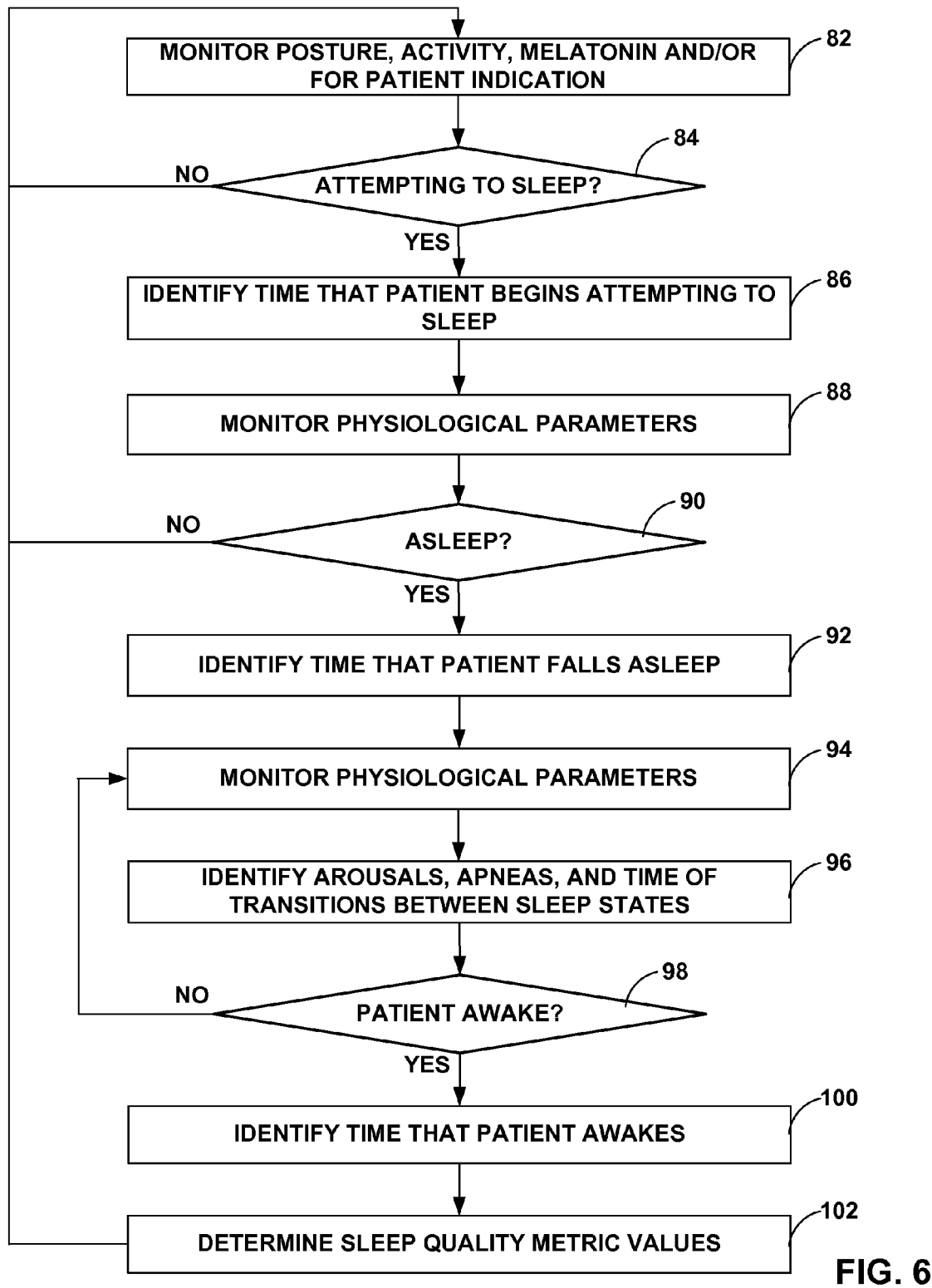
FIG. 6 is a flow diagram illustrating an example method for collecting sleep quality information that may be employed by an IMD.

FIG. 6 is a flow diagram illustrating an example method for collecting sleep quality information that may be employed by IMDs 14. In some embodiments, as discussed above, an IMD 14 may include sensors 40 that detect the posture and/or activity level of a patient 12. Furthermore, in some embodiments, IMDs 14 may include a sensor 40 that senses melatonin within one or more bodily fluids of the patients 12, such as the patient's blood, cerebrospinal fluid (CSF), or interstitial fluid. IMDs 14 may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in a patient 12, which, in turn, may cause the patient 12 to attempt to fall asleep.

An IMD 14 monitors the posture, activity level, and/or melatonin level of a patient 12, or monitors for an indication from patient 12, e.g., via patient programmer 26 (82), and determines whether patient 12 is attempting to fall asleep based on the posture, activity level, melatonin level, and/or a patient indication, as described above (84). IMDs 14 may, for example, detect an increase in the level of melatonin in a bodily fluid, and estimate the time that a patient 12 will attempt to fall asleep based on the detection. For example, IMDs 14 may compare the melatonin level or rate of change in the melatonin level to a threshold level, and identify the time that threshold value is exceeded. IMDs 14 may identify the time that a patient 12 is attempting to fall asleep as the time that the threshold is exceeded, or some amount of time after the threshold is exceeded.

If an IMD 14 determines that the patient 12 is attempting to fall asleep, the IMD 14 identifies the time that the patient 12 began attempting to fall asleep (86), and monitors one or more of the various physiological parameters of the patient 12 discussed above to determine whether the patient 12 is asleep (88, 90). For example, in some embodiments, the IMD 14 compares parameter values or parameter variability values to one or more threshold values 64 to determine whether the patient 12 is asleep. In other embodiments, the IMD 14 applies one or more functions or look-up tables to determine one or more sleep probability metric values based on the physiological parameter values, and compares the sleep probability metric values to one or more threshold values 64 to determine whether the patient 12 is asleep. Furthermore, in some embodiments an IMD 14 analyzes the amplitude and/or frequency of an EEG signal to determine when the patient is asleep, as described above with respect to FIG. 3. While monitoring physiological parameters (88) to determine whether patient 12 is asleep (90), the IMD 14 may continue to monitor the posture and/or activity level of patient 12 (82) to confirm that patient 12 is still attempting to fall asleep (84).

When the IMD 14 determines that the patient 12 is asleep, e.g., by analysis of one or more of the various parameters contemplated herein, the IMD 14 may identify the time that the patient 12 fell asleep (92). While the patient 12 is sleeping, the IMD 14 will continue to monitor physiological parameters of the patient 12 (94). As discussed above, the IMD 14 may identify the occurrence of arousals and/or apneas based on the monitored physiological parameters (96). Further, the IMD 14 may identify the time that transitions between sleep states, e.g., REM, S1, S2, S3, and S4, occur (96). For example, the IMD 14 may compare one or more sleep metric or physiological parameter values to one or more thresholds associated with the sleep states. As another example, the IMD 14 may identify a sleep state based on the prominent frequency or frequency range within an EEG of the patient, as described above with reference to FIG. 3.

Additionally, while the patient 12 is sleeping, the IMD 14 monitors physiological parameters of patient 12 (94) to determine whether patient 12 has woken up (98). When the IMD 14 determines that the patient 12 is awake, the IMD 14 identifies the time that patient 12 awoke (100), and determines sleep quality metric values based on the information collected while the patient 12 was asleep (102).

For example, one sleep quality metric value an IMD 14 may calculate is sleep efficiency, which the IMD 14 may calculate as a percentage of time during which a patient 12 is attempting to sleep that the patient 12 is actually asleep. An IMD 14 may determine a first amount of time between the time the IMD 14 identified that the patient 12 fell asleep and the time the IMD 14 identified that the patient 12 awoke. The IMD 14 may also determine a second amount of time between the time the IMD 14 identified that the patient 12 began attempting to fall asleep and the time the IMD 14 identified that the patient 12 awoke. To calculate the sleep efficiency, the IMD 14 may divide the first time by the second time.

Another sleep quality metric value that an IMD 14 may calculate is sleep latency, which the IMD 14 may calculate as the amount of time between the time the IMD 14 identified that the patient 12 was attempting to fall asleep and the time the IMD 14 identified that the patient 12 fell asleep. Other sleep quality metrics with values determined by an IMD 14 based on the information collected by the IMD 14 in the illustrated example include: total time sleeping per day, at night, and during daytime hours; number of apnea and arousal events per occurrence of sleep; and amount of time spent in the various sleep states, e.g., one or both of the S3 and S4 sleep states. An IMD 14 may store the determined values as sleep quality metric values 66 within memory 48.

An IMD 14 may perform the example method illustrated in FIG. 6 continuously, e.g., may monitor to identify when patient 12 is attempting to sleep and asleep any time of day, each day. In other embodiments, an IMD 14 may only perform the method during evening hours and/or once every N days to conserve battery and memory resources. Further, in some embodiments, an IMD 14 may only perform the method in response to receiving a command from a patient 12 or a clinician via one of programmers 20, 26. For example, a patient 12 may direct an IMD 14 to collect sleep quality information at times when the patient believes that his or her sleep quality is low or therapy is ineffective.

Sleep quality metric values determined by an IMD 14, e.g., using the method of FIG. 6, may be provided to a clinician or other user via a programmer 20, 26 or other computing device. In some embodiments, the IMD 14 may associate sleep quality metric values with the therapy or therapy parameter set in use when the values were determined. Such embodiments may provide a list of therapy parameter sets and associated sleep quality metric values to a user.

The invention is not limited to embodiments in which the therapy delivering medical device monitors the physiological parameters of the patient described herein. In some embodiments, a separate monitoring device monitors values of one or more physiological parameters of the patient instead of, or in addition to, a therapy delivering medical device. The monitor may include a processor 46 and memory 48, and may be coupled to sensors 40, as illustrated above with reference to IMDs 14 and FIGS. 2A, 2B and 3. The monitor may identify sleep and monitor sleep quality as described herein, or transmit physiological parameter information to another device, such as an IMD 14, programmer 20, 26, or other computing device for analysis of the signals to identify sleep or monitor sleep quality. In some embodiments, an external computing device, such as a programming device, may incorporate the monitor.

Figure 7:
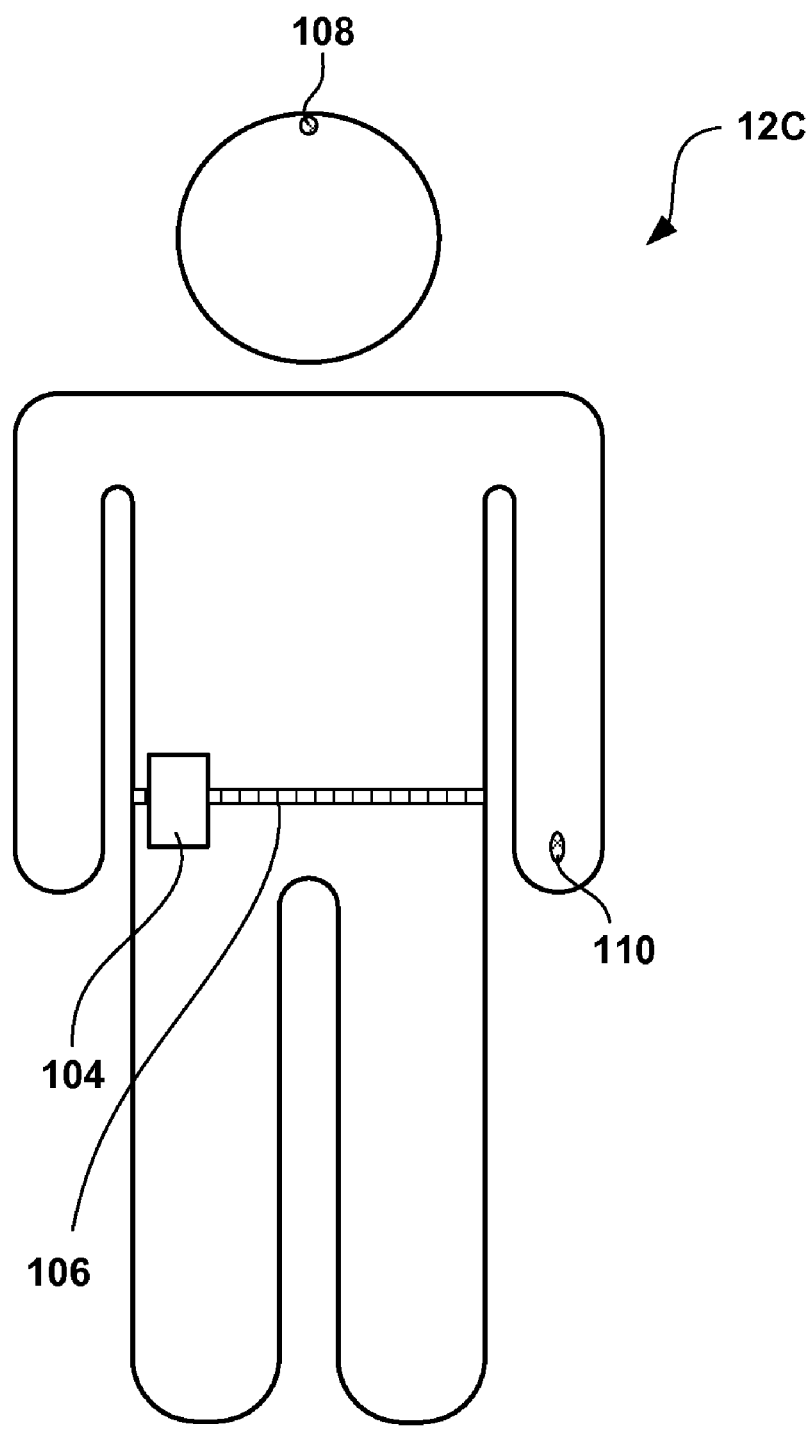
FIG. 7 is a conceptual diagram illustrating a monitor that monitors values of one or more accelerometers of the patient instead of, or in addition to, a therapy delivering medical device.

FIG. 7 is a conceptual diagram illustrating a monitor that monitors values of one or more accelerometers of the patient instead of, or in addition to, such monitoring being performed by a therapy delivering medical device. As shown in FIG. 7, patient 12C is wearing monitor 104 attached to belt 106. Monitor 104 is capable of receiving measurements from one or more sensors located on or within patient 12C. In the example of FIG. 7, accelerometers 108 and 110 are attached to the head and hand of patient 12C, respectively. Accelerometers 108 and 110 may measure movement of the extremities, or activity level, of patient 12C to indicate when the patient moves during sleep or at other times during the day. Alternatively, more or less accelerometers or other sensors may be used with monitor 104.

Accelerometers 108 and 110 may be preferably multi-axis accelerometers, but single-axis accelerometers may be used. As patient 12C moves, accelerometers 108 and 110 detect this movement and send the signals to monitor 104. High frequency movements of patient 12C may be indicative of tremor, Parkinson's disease, or an epileptic seizure, and monitor 104 may be capable of indicating to IMDs 14, for example, that stimulation therapy must be changed to effectively treat the patient. Accelerometers 108 and 110 may be worn externally, i.e., on a piece or clothing or a watch, or implanted at specific locations within patient 12C. In addition, accelerometers 108 and 110 may transmit signals to monitor 104 via wireless telemetry or a wired connection.

Monitor 82 may store the measurements from accelerometers 108 and 110 in a memory. In some examples, monitor 104 may transmit the measurements from accelerometers 108 and 110 directly to another device, such as IMDs 14, programming devices 20, 26, or other computing devices. In this case, the other device may analyze the measurements from accelerometers 108 and 110 to detect efficacy of therapy or control the delivery of therapy using any of the techniques described herein. In other embodiments, monitor 104 may analyze the measurements using the techniques described herein.

In some examples, a rolling window of time may be used when analyzing measurements from accelerometers 108 and 110. Absolute values determined by accelerometers 108 and 110 may drift with time or the magnitude and frequency of patient 12C movement may not be determined by a preset threshold. For this reason, it may be advantageous to normalize and analyze measurements from accelerometers 108 and 110 over a discrete window of time. For example, the rolling window may be useful in detecting epileptic seizures. If monitor 104 or IMDs 14 detects at least a predetermined number of movements over a 15 second window, an epileptic seizure may be most likely occurring. In this manner, a few quick movements from patient 12C not associated with a seizure may not trigger a response and change in therapy.

Figure 8:
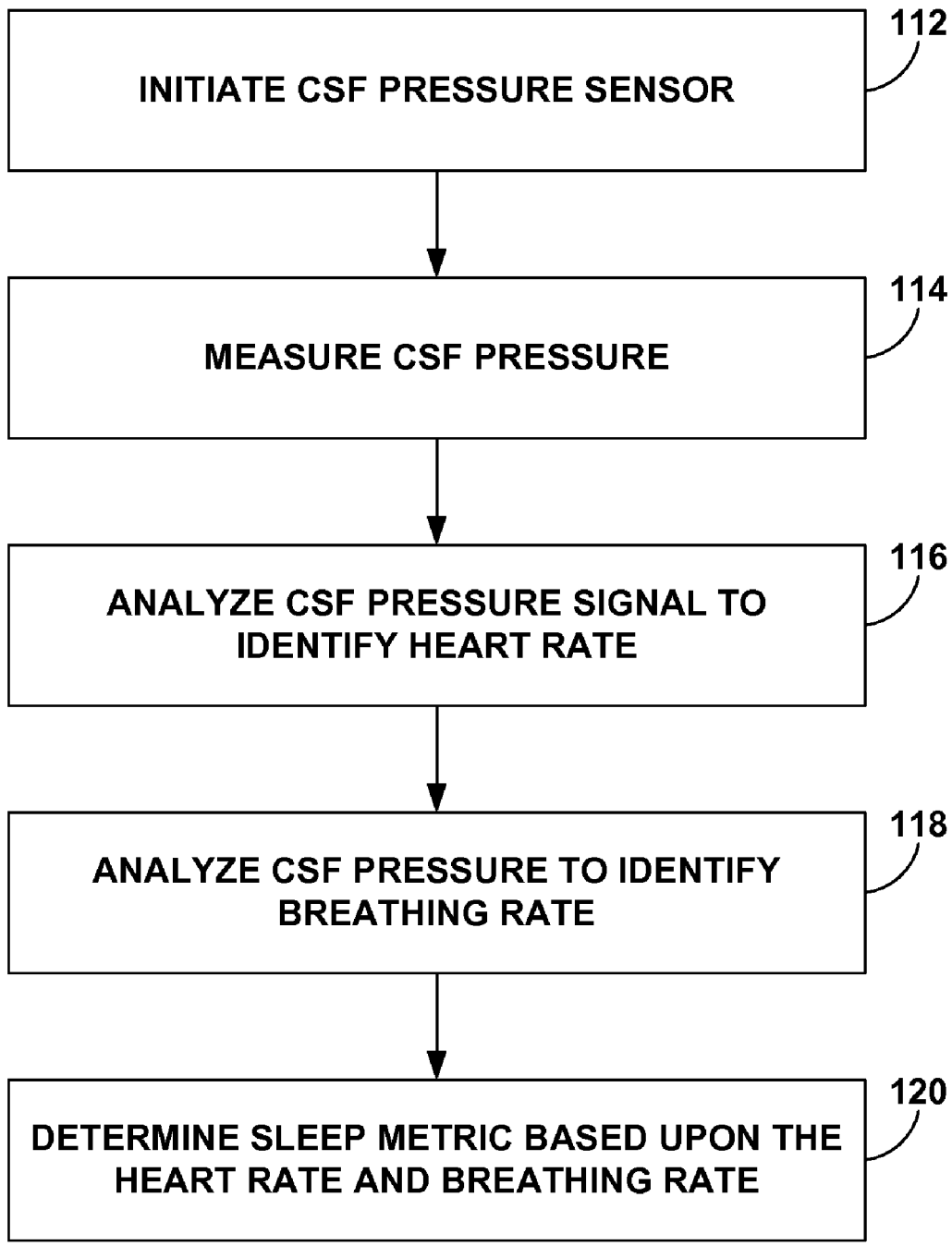
FIG. 8 is a flow diagram illustrating monitoring the heart rate and breathing rate of a patient by measuring cerebral spinal fluid pressure.

FIG. 8 is a flow diagram illustrating monitoring the heart rate and breathing rate of a patient by measuring cerebral spinal fluid pressure. As discussed above, a physiological parameter that may be measured in patient 12C is heart rate and respiration, or breathing, rate. In the example of FIG. 8, cerebral spinal fluid (CSF) pressure may be analyzed to monitor the heart rate and breathing rate of patient 12C. A clinician initiates a CSF pressure sensor to being monitoring heart rate and/or breathing rate (112). Alternatively, the CSF pressure sensor may be implanted within the brain or spinal cord of patient 12C to acquire accurate pressure signals. The CSF pressure sensor must also store the pressure data or begin to transfer pressure data to an implanted or external device. As an example used herein, the CSF pressure sensor transmits signal data to an IMD 14.

Once the CSF pressure sensor is initiated, the CSF pressure sensor measures CSF pressure and transmits the data to IMD 14 (114). The IMD 14 analyzes the CSF pressure signal to identify the heart rate (116) and breathing rate (118) of patient 12C. The heart rate and breathing rate can be identified within the overall CSF pressure signal. Higher frequency fluctuations (e.g. 40 to 150 beats per minute) can be identified as the heart rate while lower frequency fluctuations (e.g. 3 to 20 breaths per minute) in CSF pressure are the breathing rate. An IMD 14 may employ filters, transformations, or other signal processing techniques to identify the heart rate and breathing rate from the CSF pressure signal. IMDs 14 may utilize the heart rate and breathing rate information as additional information when determining the sleep metric of patient 12C (120).

Various embodiments of the invention have been described. However, one skilled in the art will appreciated that various modifications may be made to the described embodiments without departing from the scope of the invention. For example, although described herein in the context of an implantable neurostimulator, the invention may be embodied in any implantable or external device. Further, the invention may be embodied in devices that treat any a variety of disorders of the patient.

As discussed above, the ability of a patient to experience quality sleep, e.g., the extent to which the patient able to achieve adequate periods of undisturbed sleep in deeper, more restful sleep states, may be negatively impacted by any of a variety of ailments or symptoms. Accordingly, the sleep patterns or sleep quality of a patient may reflect the progression, status, or severity of the ailment or symptom. Further, the sleep patterns or quality of the patient may reflect the efficacy of a particular therapy or therapy parameter set in treating the ailment or symptom. In other words, it may generally be the case that the more efficacious a therapy or therapy parameter set is, the higher quality of sleep the patient will experience.

As discussed above, in accordance with the invention, systems may use the sleep detection techniques of the invention to monitor sleep quality or sleep patterns, which may be used to evaluate the status, progression or severity of an ailment or symptom, or the efficacy of therapies or therapy parameter sets used to treat the ailment or symptom. As an example, chronic pain may cause a patient to have difficulty falling asleep, experience arousals during sleep, or have difficulty experiencing deeper sleep states. Systems according to the invention may monitor sleep to evaluate the extent to which the patient is experiencing pain.

In some embodiments, systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to determine when the patient is asleep or in certain sleep states, monitor sleep patterns based on such sleep state information, and thereby facilitate evaluation of any of the above-identified therapies. Systems according to the invention may thereby evaluate the extent to which a therapy or therapy parameter set is alleviating chronic pain by evaluating the extent to which the therapy or therapy parameter set improves sleep quality or patterns for the patient.

As another example, psychological disorders may cause a patient to experience low sleep quality. Accordingly, embodiments of the invention may monitor sleep or sleep states that sleep quality to track the status or progression of a psychological disorder, such as depression, mania, bipolar disorder, or obsessive-compulsive disorder. Further, systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to associate sleep pattern or quality information with the therapies or therapy parameter sets for delivery of such therapies, and thereby evaluate the extent to which a therapy or therapy parameter set is alleviating the psychological disorder by evaluating the extent to which the therapy parameter set improves the sleep quality of the patient.

Movement disorders, such as tremor, Parkinson's disease, multiple sclerosis, spasticity, or epilepsy, may also affect sleep patterns and the sleep quality experienced by a patient. The uncontrolled movements, e.g., tremor or shaking, associated such disorders, particularly in the limbs, may cause a patient to experience disturbed sleep. Accordingly, systems according to the invention may monitor sleep, sleep states, sleep patterns, or sleep quality of the patient to determine the state or progression of a movement disorder. Both psychological disorders and movement disorders are examples of neurological disorders that may afflict a patient 12.

Further, systems according to the invention may include any of a variety of medical devices that deliver any of a variety of therapies to treat a movement disorders, such as DBS, cortical stimulation, or one or more drugs. Baclofen, which may or may not be intrathecally delivered, is an example of a drug that may be delivered to treat movement disorders. Systems may use the techniques of the invention described above to associate sleep pattern or quality information with therapies or therapy parameter sets for delivery of such therapies. In this manner, such systems may allow a user to evaluate the extent to which a therapy or therapy parameter set is alleviating the movement disorder by evaluating the extent to which the therapy parameter set improves the sleep quality experienced by the patient.

As another example, although described in the context of determining whether a patient is asleep, e.g., whether the patient's current sleep state is asleep or awake, the invention may, as described above, be used to determine what level of sleep a patient is currently experiencing, e.g., which of sleep states REM, S1, S2, S3, and S4 the patient is currently in. A medical device may record transitions between these states and between sleep and wakefulness, or may control therapy based on transitions between these states and between sleep and wakefulness. Further, in some embodiments, a medical device may, without making a sleep determination, simply record one or more determined sleep metric values for later analysis, or may control delivery of therapy based on the sleep metric values.

Further, the invention may be embodied in a programming device, such as programmers 20, 26 described above, or another type of computing device. In particular, in some embodiments, a computing device may determine when a patient 12 is asleep according to the invention instead of, or in addition to an implantable or external medical device. For example, a medical device may record values for one or more of the physiological parameters discussed herein, and may provide the physiological parameter values to the computing device in real time or when interrogated by the computing device. The computing device may apply the techniques described herein with reference to IMDs 14 to determine when a patient 12 is asleep, and may control delivery of therapy based on the determination, or present information relating to the patient's sleep patterns to a user to enable diagnosis or therapy evaluation. The computing device may be a programming device, such as programmers 20, 26, or may be any handheld computer, desktop computer, workstation, or server. A computing device, such as a server, may receive information from the medical device and present information to a user via a network, such as a local area network (LAN), wide area network (WAN), or the Internet.

The invention may also be embodied as a computer-readable medium, such as memory 48, that includes instructions to cause a processor, such as processor 46, to perform any of the methods described herein. These and other embodiments are within the scope of the following claims.

What is claimed is:

1. A method for evaluating an efficacy of a movement disorder therapy comprising:
    monitoring at least one physiological parameter of a patient via an implantable medical device that delivers the movement disorder therapy to the patient;
    monitoring sleep patterns of the patient with the implantable medical device based on the physiological parameter;
    determining sleep quality information based on the sleep patterns; and
    presenting the sleep quality information in conjunction with information regarding the delivery of the movement disorder therapy to a user to allow the user to evaluate the efficacy of the movement disorder therapy,
    wherein the movement disorder therapy delivered by the implantable medical device to the patient treats a movement disorder selected from a group consisting of:
    tremor;
    Parkinson's disease;
    multiple sclerosis;
    spasticity; and
    epilepsy.

2. The method of claim 1, wherein monitoring sleep patterns comprises: determining a value of a sleep probability metric that indicates a probability of the patient being asleep based on the physiological parameter; and
    determining whether the patient is asleep based on the sleep probability metric value.

3. The method of claim 2,
    wherein monitoring at least one physiological parameter comprises monitoring a plurality of physiological parameters,
    wherein determining a value of a sleep probability metric comprises determining a value for each of a plurality of sleep probability metrics that each indicate a probability of the patient being asleep, each of the values determined based on a respective one of the physiological parameters, and
    wherein determining whether the patient is asleep comprises determining whether the patient is asleep based on the plurality of sleep probability metric values.

4. The method of claim 3, wherein determining whether the patient is asleep based on the plurality of sleep probability metric values comprises:
    applying a weighting value to at least one of the sleep probability metric values; and
    determining a value of an overall sleep probability metric based on the plurality of sleep probability metric values.

5. The method of claim 2, further comprising comparing the value of the sleep probability metric to a plurality of thresholds, wherein monitoring sleep patterns of the patient comprises determining a sleep state of the patient based on the comparison.

6. The method of claim 5, wherein determining a sleep state of the patient comprises determining whether the patient is in one of an S3 or S4 sleep state.

7. The method of claim 1,
wherein monitoring at least one physiological parameter of a patient comprises monitoring an electroencephalogram (EEG) of the patient, and
wherein monitoring sleep patterns of the patient comprises determining a sleep state of the patient based on a frequency of the EEG.

8. The method of claim 7, wherein determining a sleep state of the patient comprises determining whether the patient is in one of an S3 or S4 sleep state.

9. The method of claim 1, further comprising:
determining a value of a sleep quality metric based on the sleep patterns, wherein presenting the sleep quality information in conjunction with information regarding the delivery of the movement disorder therapy to the user comprises presenting the value of the sleep quality metric to the user; and
associating the value of the sleep quality metric with a therapy parameter set used to deliver the movement disorder therapy to the patient when the sleep quality metric value was determined, wherein presenting the sleep quality information in conjunction with information regarding the delivery of the movement disorder therapy to the user comprises presenting the value of the sleep quality metric and the associated therapy parameter set to the user.

10. The method of claim 1, further comprising associating the sleep quality information with a therapy parameter set used to deliver the movement disorder therapy to the patient when the sleep quality information was determined, wherein presenting the sleep quality information in conjunction with information regarding the delivery of the movement disorder therapy to the user comprises presenting the sleep quality information and the associated therapy parameter set to the user.

11. The method of claim 1, wherein the movement disorder therapy delivered by the implantable medical device to the patient includes deep brain stimulation.

12. The method of claim 1, wherein the movement disorder therapy delivered by the implantable medical device to the patient treats tremor.

13. A medical system comprising:
a sensor that generates a signal as a function of at least one physiological parameter of a patient;
an implantable medical device that delivers a movement disorder therapy, monitors the at least one physiological parameter of the patient based on the signal output by the sensor, and monitors sleep patterns of the patient based on the physiological parameter;
a processor that determines sleep quality information based on the sleep patterns for evaluation of an efficacy of the movement disorder therapy; and
a computing device that provides the sleep quality information in conjunction with information regarding the delivery of the movement disorder therapy to a user to allow the user to evaluate the efficacy of the movement disorder therapy,
wherein the movement disorder therapy delivered by the implantable medical device to the patient treats a movement disorder selected from a group consisting of:
tremor;
Parkinson's disease;
multiple sclerosis;
spasticity; and
epilepsy.

14. The medical system of claim 13, wherein the processor determines a value of a sleep probability metric that indicates a probability of the patient being asleep based on the physiological parameter, and determines whether the patient is asleep based on the sleep probability metric value.

15. The medical system of claim 14,
further comprising a plurality of sensors, each of the sensors generating a respective signal as a function of at least one of a plurality of physiological parameters,
wherein the processor monitors the plurality of physiological parameters, determines a value for each of a plurality of sleep probability metrics that each indicate a probability of the patient being asleep, each of the values determined based on a respective one of the physiological parameters, and determines whether the patient is asleep based on the plurality of sleep probability metric values.

16. The medical system of claim 15, wherein the processor applies a weighting value to at least one of the sleep probability metric values, and determines a value of an overall sleep probability metric based on the plurality of sleep probability metric values.

17. The medical system of claim 14, wherein the processor compares the value of the sleep probability metric to a plurality of thresholds, and monitors sleep patterns by determining a sleep state of the patient based on the comparison.

18. The medical system of claim 17, wherein the processor determines whether the patient is in one of an S3 or S4 sleep state.

19. The medical system of claim 13,
wherein the sensor comprises an electrode coupled to the implantable medical device,
wherein the implantable medical device monitors an electroencephalogram (EEG) of the patient via the electrode, and
wherein the processor monitors sleep patterns of the patient by determining a sleep state of the patient based on a frequency of the EEG.

20. The medical system of claim 19, wherein the processor determines whether the patient is in one of an S3 or S4 sleep state.

21. The medical system of claim 13, wherein the implantable medical device comprises at least one of an implantable neurostimulator or an implantable pump.

22. The medical system of claim 13,
wherein the processor associates the sleep quality information with a therapy parameter set used to deliver the movement disorder therapy to the patient when the sleep quality information was determined, and
wherein the computing device provides the sleep quality information and the associated therapy parameter set to the user.

23. The medical system of claim 13, wherein the movement disorder therapy delivered by the implantable medical device to the patient includes deep brain stimulation.

24. The medical system of claim 13, wherein the movement disorder therapy delivered by the implantable medical device to the patient treats epilepsy.

25. A medical system comprising:
means for monitoring at least one physiological parameter of a patient via an implantable medical device that delivers a movement disorder therapy to the patient;
means for monitoring sleep patterns of the patient with the implantable medical device based on the physiological parameter;
means for determining sleep quality information based on the sleep patterns for evaluation of an efficacy of the movement disorder therapy; and means for presenting the sleep quality information in conjunction with information regarding the delivery of the movement disorder therapy to a user to allow the user to evaluate the efficacy of the movement disorder therapy, wherein the movement disorder therapy delivered by the implantable medical device to the patient treats a movement disorder selected from a group consisting of:
tremor;
Parkinson's disease;
multiple sclerosis;
spasticity; and
epilepsy.

26. The medical system of claim 25, wherein the means for monitoring sleep patterns comprises means for determining a value of a sleep probability metric that indicates a probability of the patient being asleep based on the physiological parameter.

27. The medical system of claim 25, wherein the means for monitoring sleep patterns comprises means for identifying whether that patient is in at least one of a S1, S2, S3, S4 or rapid eye movement (REM) sleep state.

28. The medical system of claim 25, further comprising means for associating the sleep quality information with a therapy parameter set used to deliver the movement disorder therapy to the patient when the sleep quality information was determined.

29. The medical system of claim 25, wherein the movement disorder therapy delivered by the implantable medical device to the patient includes deep brain stimulation.

30. The medical system of claim 25, wherein the movement disorder therapy delivered by the implantable medical device to the patient treats spasticity.

* * * * *